US009713446B2

(12) United States Patent
Gal et al.

(10) Patent No.: US 9,713,446 B2
(45) Date of Patent: Jul. 25, 2017

(54) EAR CLIP FOR MEDICAL MONITORING DEVICE

(71) Applicant: A.D. Integrity Applications Ltd., Ashdod (IL)

(72) Inventors: Avner Gal, Hertzliya (IL); David Malka, Rehovot (IL); Vladimir Ravitch, Ashkelon (IL); Alexander Klionsky, Ashdod (IL); Vitaly Bondar, Ashdod (IL)

(73) Assignee: A.D. Intergrity Applications Ltd., Ashdod (IL)

( * ) Notice: Subject to any disclaimer, the term of this patent is extended or adjusted under 35 U.S.C. 154(b) by 0 days.

(21) Appl. No.: 15/386,394

(22) Filed: Dec. 21, 2016

(65) Prior Publication Data

US 2017/0112442 A1    Apr. 27, 2017

Related U.S. Application Data

(63) Continuation of application No. 14/421,002, filed as application No. PCT/IL2014/050218 on Mar. 5, 2014, now abandoned.

(30) Foreign Application Priority Data

Mar. 12, 2013   (IL) .......................................... 225182

(51) Int. Cl.
*F16B 2/10*   (2006.01)
*A61B 5/05*   (2006.01)
(Continued)

(52) U.S. Cl.
CPC .............. *A61B 5/6816* (2013.01); *A61B 5/01* (2013.01); *A61B 5/05* (2013.01); *A61B 5/14532* (2013.01);
(Continued)

(58) Field of Classification Search
CPC .............. A61B 5/6816; A61B 5/14532; A61B 5/14552; A61B 5/443; A61B 5/6826; A61B 5/6838; A61B 5/6819
(Continued)

(56) References Cited

U.S. PATENT DOCUMENTS 3,177,542 A   4/1965   James
4,616,384 A   10/1986  Lowell et al.
(Continued)

FOREIGN PATENT DOCUMENTS

AU   2014229190 B   2/2016
CN   2295488 B      10/1998
(Continued)

OTHER PUBLICATIONS

PCT/IL2014/050218, Written Opinion of the International Search Authority, Mailed Jun. 22, 2014.
(Continued)

*Primary Examiner* — Robert J Sandy
*Assistant Examiner* — Rowland Do
(74) *Attorney, Agent, or Firm* — Wiggin and Dana LLP; Gregory S. Rosenblatt

(57) ABSTRACT

A hinge pin joint for facilitating precise separation of the jaws of a spring clip, including a base cylinder with a threaded bore, supports extending laterally out from the base cylinder, pin supports capable of pivoting, and stabilizing wings extending from the pin supports. In one embodiment, the capability of pivoting includes pins that are integral with the pin supports and which extend out laterally from the pin support. An alternate embodiment includes aligned opening in the pin supports into which pins may be inserted. At least one stopper may be disposed on at least one of the pin supports for supporting the upper shell. The stabilizing
(Continued)

wings are configured as plates that are semi-rigidly secured in guide structures within the lower shell.

12 Claims, 22 Drawing Sheets

(51) Int. Cl.
  *A61B 8/00* (2006.01)
  *A61B 5/00* (2006.01)
  *A61B 5/145* (2006.01)
  *A61B 5/01* (2006.01)

(52) U.S. Cl.
  CPC .............. *A61B 8/4209* (2013.01); *F16B 2/10* (2013.01); *A61B 2560/0228* (2013.01)

(58) Field of Classification Search
  USPC .......... 24/509, 500, 499, 502, 505; 600/365, 600/309, 323, 344
  See application file for complete search history.

(56) References Cited

U.S. PATENT DOCUMENTS

| | | | |
|---|---|---|---|
| 4,685,464 A | 8/1987 | Goldberger et al. | |
| 5,247,931 A | 9/1993 | Norwood | |
| 5,792,052 A | 8/1998 | Isaacson et al. | |
| 6,041,247 A | 3/2000 | Weckstrom et al. | |
| 6,385,821 B1 | 5/2002 | Modgil et al. | |
| 6,842,951 B1 | 1/2005 | Barre et al. | |
| 7,937,129 B2 | 5/2011 | Mason et al. | |
| 8,073,518 B2 | 12/2011 | Chin | |
| 8,235,897 B2 | 8/2012 | Gal et al. | |
| 8,588,880 B2 | 11/2013 | Abdul-Hafiz et al. | |
| 8,897,850 B2 | 11/2014 | Jochim et al. | |
| 2001/0009265 A1 | 7/2001 | Schulz et al. | |
| 2001/0045532 A1 | 11/2001 | Schulz et al. | |
| 2002/0156354 A1 | 10/2002 | Larson | |
| 2004/0054291 A1 | 3/2004 | Schulz et al. | |
| 2005/0033131 A1 | 2/2005 | Chen et al. | |
| 2007/0032711 A1 | 2/2007 | Coakley et al. | |
| 2007/0260131 A1 | 11/2007 | Chin | |
| 2011/0263956 A1 | 10/2011 | Gal et al. | |
| 2011/0295092 A1 | 12/2011 | Tatara et al. | |
| 2013/0218025 A1 | 8/2013 | Tverskoy | |

FOREIGN PATENT DOCUMENTS

| | | |
|---|---|---|
| KR | 101640910 B | 8/2016 |
| WO | 2011135562 A2 | 11/2011 |

OTHER PUBLICATIONS

PCT/IL2014/050218, International Preliminary Report on Patentability, Mailed Dec. 29, 2014.
The State Intellectual Property Office of the People's Republic of China, CN 201480001799.4, the First Office Action, Dec. 2015.
European Patent Office, EP 14 763 133.7, Communication under Rule 71.3 (EPC), Intention to Grant, Nov. 2016.

Fig. −19

EAR CLIP FOR MEDICAL MONITORING DEVICE

CROSS-REFERENCE TO RELATED PATENT APPLICATIONS

This patent application is a continuation of U.S. patent application Ser. No. 14/421,002 titled, "Ear Clip for Medical Monitoring Device," by Gal et al., that was filed on Feb. 11, 2015. U.S. Ser. No. 14/421,002 is a national stage patent application filed under the provisions of 35 U.S.C. §371 based on PCT/IL2014/050218, filed Mar. 5, 2014 that claims priority to Israeli patent application number IL 225182, filed Mar. 12, 2013. The disclosure of U.S. Ser. No. 14/421,002 is incorporated by reference herein in its entirety.

BACKGROUND

This invention relates to medical diagnosis, and more particularly, to an ear clip that allows a medical measuring device to be attached to an ear lobe.

Modern medicine today is driven by miniaturization and non-invasive and minimally invasive methods for surgery, examination, diagnosis and and/or monitoring. There is a desire to make examination and treatment faster and cheaper. The use of non-invasive techniques reduces pain for the patient and reduces risk of infection.

Patient monitoring is a key aspect of modern medicine. Monitors of different types are available for monitoring different body functions and parameters. Such monitors interact with the body to receive and data concerning the body functions for processing.

Blood monitoring devices are conveniently affixed to the earlobe. Most typically this is accomplished with a clip. This clip may be a type of spring clip, wherein the jaws of the clip are forced together by a spring to attach to the earlobe. When levers of extending from the two jaws past an axle are pinched together, the jaws may be separated, thereby releasing the ear lobe, so that the clip can be removed. When pressure forcing these levers together is released, the spring draws the jaws together, to grip the earlobe.

A problem with this basic clip design is that the separation between the closed jaws is not precisely determined. Consequently, the basic clip is not suitable for applications which require a precisely determined jaw separation. Furthermore, if the pressure is too tight, it may flatten capillaries and adversely affect the blood flow and other blood related parameters that are being monitored. A clip should firmly engage the ear-lobe without squeezing it sufficiently to affect the readings.

Many non-invasive medical monitoring devices need to be reliably attached to the body so that accurate readings may be taken. These devices sometimes need to be adjusted to the individual body.

In the case of devices that are attached to the earlobe, some devices require that the distance between the sensing elements be adapted to the individual thickness of the earlobe of the patient. Such devices are also required to easily open and close for attaching and releasing the clip from the ear lobe. For diagnostic reliability, the manufacturing tolerances are high, and parts have to be manufactured to high precision.

With moving parts, particularly where several different independent movements take place at the same time in a small device and the required precision is very high, for example ±5 microns in position, whilst maintaining jaw parallelism common production standards of around 100 microns are insufficient. Thus, for accurate measurements, there is a need for a reliable ear clip that can be accurately fitted to a patient's ear lobe with a known but adjustable jaw separation. Such a clip is required to be reliable and easily mass produced.

SUMMARY OF THE INVENTION

A first aspect of the invention is directed to providing a clip comprising: an upper shell and a lower shell coupled together around a hinge pin, the upper and lower shells having a pair of jaws on a first side of the hinge pin and handles for squeezing together to separate the jaws on a second side of the hinge pin; a biasing spring to oppose the squeezing together of the handles and to urge the jaws together and at least one stop to prevent the jaws from closing completely and to keep the jaws in parallel alignment when no force is applied to handles to overcome the biasing force of the spring and an adjustment mechanism to adjust the separation of the jaws.

Preferably, the adjustment mechanism comprises an adjustment screw, a washer clip, and an insert; said adjustment screw having a screw head and a threaded shank, the shank being pushed through a clearance hole in the lower shell and the adjustment screw being held in place around the lower shell by the washer clip, the insert for fitting into a recess in the upper shell; said hinge pin being attached to said insert; said insert comprising a central block with a tapped hole therein, radial arms extending from the central block, and stabilizing wings integrally cast with the central block and radial arms; the stabilizing wings at an angle to the radial arms; said stabilizing wings for engaging the upper shell in accurate alignment with the lower shell; wherein the tapped hole is for receiving the adjustment screw such that the tapped hole and adjustment screw enables adjustment of the separation between the jaws of the upper shell and the lower shell when biasing effect of the biasing spring is not opposed by a squeezing pressure on handles.

Typically, the clip is for clipping onto an ear lobe.

The clip typically further comprises blood parameter sensors mounted in said jaws.

Optionally, the stabilizing wings are plates that have an axis that is parallel to an axis of the screw.

Optionally, the stabilizing wings converge slightly towards an axis mutually perpendicular to the axes of the hinge pin and the axis of the adjustment screw.

In one embodiment, the hinge pin is integral to the insert.

In an alternative embodiment, the hinge pin engages holes in said insert and holes in said upper shell to connect said upper shell to said insert.

Optionally, the stop is a part of the insert.

In an alternative embodiment, the stop is part of the lower shell.

In one embodiment, the biasing spring is a helical spring and ends of said biasing spring bear against the back of the pin supports and middle section of said spring bears against an inner surface of said upper shell to urge jaws together.

In another embodiment, the biasing spring is wrapped around said hinge pin.

A second aspect is directed to an adjustment mechanism for a clip comprising two shells coupled by a hinge pin, for adjusting a separation between jaws of said clip when biased towards each other by a spring, the adjustment mechanism comprising a screw threaded through and locked to one shell and an insert attached to a second shell having a threaded bore for engaging said screw.

Optionally, the insert comprises stabilizing wings that are parallel to said bore and separated from the bore by radial arms, and where the stabilizing wings are restrained by corresponding socket slots in said shell.

In one embodiment, the screw is locked to one shell with a washer clip that slides onto and springingly engages shank of said screw.

BRIEF DESCRIPTION OF THE DRAWINGS

For a better understanding of the invention, its operating and specific objects attained by its uses, references should be had to accompanying drawings and descriptive matter in which there are illustrated preferred embodiments of the invention.

The invention will now be described in connection with certain preferred embodiments with reference to the following illustrative figures so that it may be more fully understood.

Figure 1:
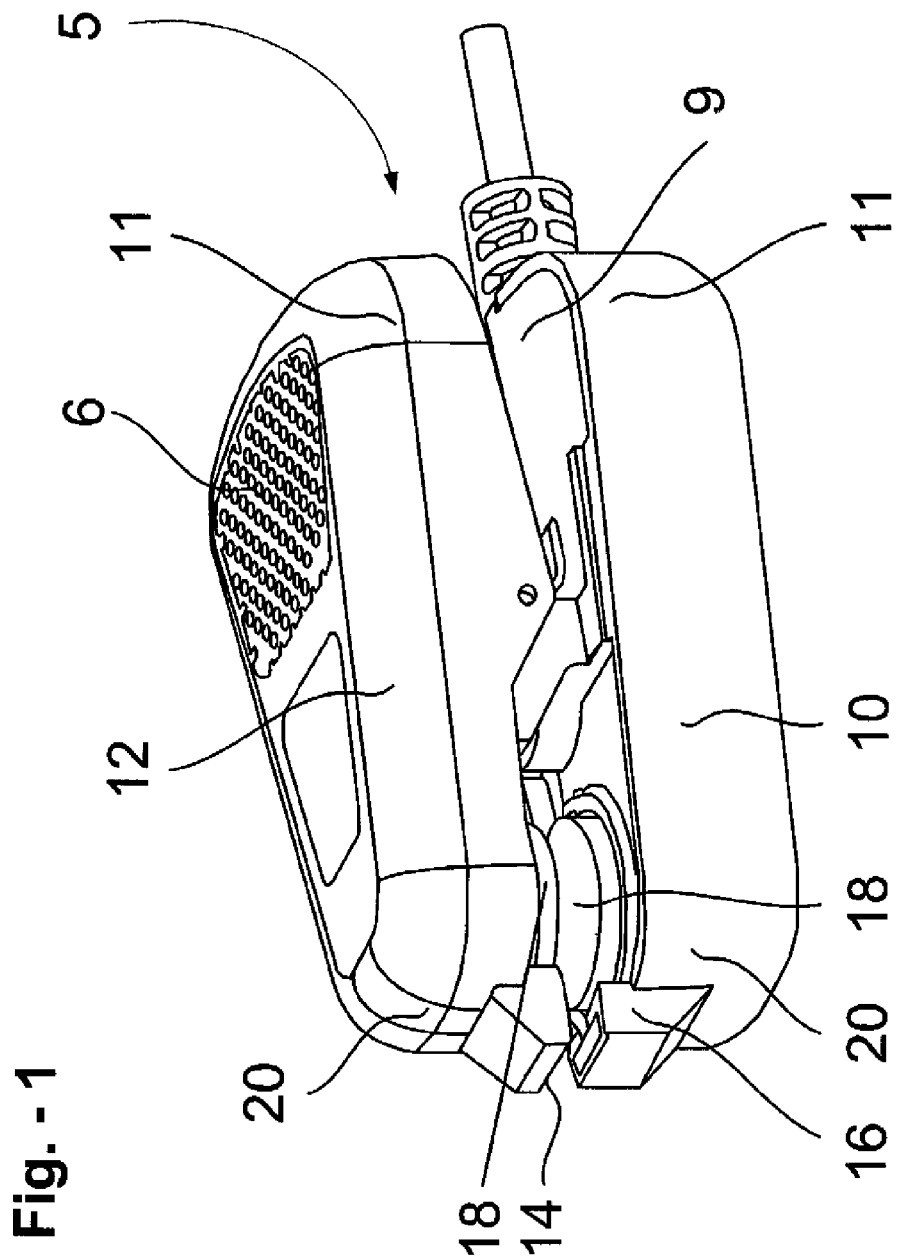
FIG. 1 is a perspective view of the ear clip in a closed configuration.

Consistent numbering is generally used in the various images and embodiments.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

An advantage of the clip of the invention is that it achieves high precision within a small mechanical size.

A main feature is that the jaws of the clip do not close together such that they touch, but rather close such that they are parallel and separated by a known gap.

Preferably the gap is adjustable by an adjusting mechanism so that it can be configured to engage a tissue of a patient, such as an ear lobe, for example.

Other objects, features and advantages of the present invention will become apparent upon reading the following detailed description in conjunction with the drawings and the claims.

An embodiment of the invention relates to an ear clip whose ear lobe engaging jaws may be opened around an axis, and whose jaw separation may be controlled with high accuracy and precision. This is accomplished by an insert having a v-shaped cross section that fits into a guide assembly.

An aspect of the invention is directed to a hinge pin joint comprising: a base cylinder with a threaded bore; supports extending laterally out from said base cylinder; pin supports having means for pivoting; and wings extending from said supports. In the preferred embodiment, the means for pivoting includes pins made integral with the pin supports and extending out laterally. An alternate embodiment includes aligned openings in the pin supports into which pins are inserted. At least one stopper may be disposed on at least one of the pin supports and the stopper helps to support an upper shell. The support wings may be configured as plates that are semi-rigidly secured in guide structures in a lower shell.

An embodiment of the invention is directed to a clip comprising upper and lower shells that are affixable to a body. The clip comprises a hinge pin joint that includes a base cylinder with a threaded bore; supports extending laterally out from said base cylinder; pin supports having means for pivoting; and wings extending from said supports and semi-rigidly positioned in a cavity of the lower shell. In a preferred embodiment, the means for pivoting includes pins that are an integral part of the pin supports and extend laterally from the pin supports. An alternate embodiment includes aligned openings in the pin supports into which hinge pins are inserted. Distal ends of the hinge pin are secured within mountings on the upper shell. An adjustment screw is secured to the lower shell and threaded into a bore within the base cylinder. At least one stopper may be disposed on at least one of the pin supports for supporting the upper shell. The support wings are configured as plates that are semi-rigidly secured in guide structures within the lower shell.

This ear clip is a spring clamp that consists of a pair of jaws that may be opened by a squeezing action on handles that server as levers. The ear clip comprises two sections that each consist a jaw and a handle. The two sections are joined together such that they may pivot, by an axle pin. The clip further comprises a spring that operates on the hinge and serves to urge the jaws together. Pressure on the handles separates the jaws.

The hinge is positioned so that jaws in front of the hinge are separated when the parts of the ear clip behind the hinge (the handles) are pressed A spring is positioned to keep the ear clip in a closed position by urging the jaws together and the handles apart. To prevent the ear clip from closing completely, a simple stopper or stopping mechanism is built into the design. The stopper allows the ear clip to close in such a manner that the jaws (the sides of the ear clip that are on the ear lobe) are parallel to each other about the ear lobe at all separations to be measured between the sensors. This is in contrast to known clips, wherein the jaws tilt towards each other and meet at a line when fully closed, such that, for each jaw separation, the angle of the jaws is different, and the jaws slope. The jaws of the clip of the present invention are parallel to each other and may be fastened around an ear lobe.

The two parts of the ear clip can be adjusted with respect to each other so that, when they are in a closed position, the distance between the two parallel jaws can be set to a known desired separation (either more or less), in order to fit to the thickness of a specific patient's earlobe.

This arrangement allows positioning a number of sensors in the tips of each half such that they remain parallel to each other. Otherwise, the jaws would close to an unknown separation that depends on the individual thickness of the ear lobe and the strength of the spring, and, instead of being parallel, the jaws and sensors therein would be at an angle. Even when a stop is used that prevents the two halves from closing completely, it is possible that a thicker than usual ear lobe will not allow the two halves to close until they reach in their closing movement the stop, thus also leading to a situation where the sensors on the two halves are not exactly parallel to each other, but instead are at a small angle. The consequence of such angled sensors would lead to differences of measurement due to differences of relative positions of the sensors, depending on each patient's individual earlobe.

The two halves of the device are hollow and also serve as the housing for the electronic components, and hold the base of the sensors and an adjustment mechanism.

According to the invention, the hinge pin coupling the two parts is mounted on a separate component that is connected to a dedicated adjustment mechanism that is typically a screw that allows the adjustment of the separation between the sensors at the tip of the clip in a closed position and also allows the two halves of the clip to be opened when the handles are pressed and closed by the spring when the handles are released.

A difficulty in clip construction of an ear clip for monitoring blood parameters of blood vessels in the ear lobe is that manufacturing clearances are needed to allow the clip to be opened and closed. Keeping the necessary minimum clearance between moving parts, however, leads to less precision concerning the exact parallelism and position of the sensors in the tip end (jaws) of the clip. Because the sensors are positioned in the jaws of the clip, inaccuracies resulting from the required clearance in the middle section of the clip (i.e. around the axle) that is necessary for the movement of the parts is magnified as one moves from the axle towards the jaws and results in a bigger inaccuracy in the jaws where the sensors are mounted.

In addition to the necessary clearance to allow movement, manufacturing inaccuracies may lead to a further decrease of precision. Such manufacturing inaccuracies may lead to parts that fit together too tightly to be easily moved, or that are too loose to maintain the necessary precision and parallelism for holding sensors.

Thus there is a need to allow the jaws to be opened and closed easily, whilst nevertheless enabling accurate control of the separation of the jaws.

These problems of clearances, accuracy and precision during production are overcome by the introduction of specially formed male and female parts. These specially formed parts compensate for the required tolerances and manufacturing inaccuracies, whilst achieving the desired jaw separation precision.

Figure 2:
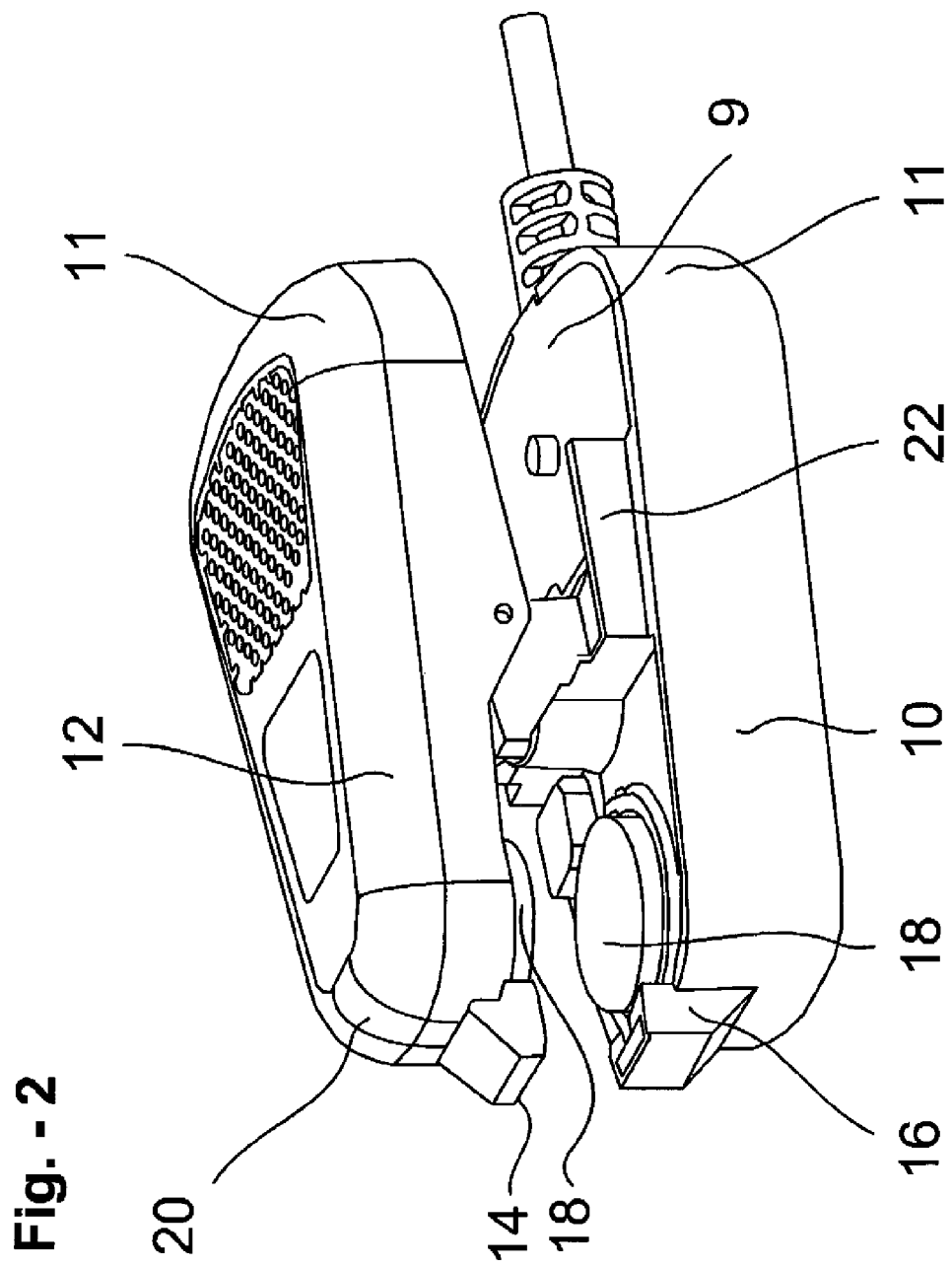
FIG. 2 is a perspective view of the ear clip from the angle of FIG. 1, but with the two shells at maximum separation.

Referring now to FIGS. 1 and 2 an ear clip 5 is shown. The ear clip 5 includes lower and upper shells 10, 12 in which various sensor components are housed. As will be hereinafter explained, the shells 10, 12 pivot with respect to each. This pivoting action allows jaws 20 at the ends of the shells to be separated to facilitate placement on the earlobe.

If desired, the surfaces of the shells 10, 12 may include non-slip pads 6, perhaps with a texture, to facilitate gripping.

The shells 10, 12 may be fabricated from a wide range of suitable materials. In preferred embodiments, the shells 10, 12 fabricated from plastic and, may be injection moulded, for example.

A number of sensors may be positioned within the jaws 20 of the shells 10, 12, depending on the parameters to be monitored or measured. In one implementation, the ear clip 5 is used for non-invasively measuring glucose in the blood stream and appropriate sensing elements are required. Details of appropriate sensors may be found in issued U.S. Pat. No. 8,235,897, co-pending U.S. patent application Ser. No. 13/540,656 and International application PCT/IL2001/000328). In this implementation, a thermal sensor 14 for the thermal measuring channel is located on the tip 16 of one of the shells in the drawing it is in on the lower shell 10, it may, however, 1 and 2 contain it placed on the lower shell) of the ear clip 5. Membranes 18 may also be provided. These membranes 18 serve to house piezo-electrical transducers (such as a transmitter and a receiver) for an ultrasonic measuring channel, for example. The membranes 18 may also serve as capacitor plates for an electromagnetic measurement channel, for example.

The specific sensors and monitoring elements are, however, not pertinent to the invention that is described and claimed herein. Any desirable combination of sensors and monitoring elements may be utilized in the ear clip 5. Sensor 14 and sensor 18 shown and described are for illustrative purposes only. Any suitable support structure may be utilized in the shells for the electronic components.

It will be appreciated that depending on the sensors and monitoring elements that are used and the accuracy of measurement required, certain parameters and orientations need to be maintained for proper and accurate operation of the ear clip 5 as a tool for measuring blood parameters. In particular, for the aforementioned non-invasive glucose monitor, the membranes 18 need to be oriented precisely with respect to each other in order to obtain accurate readings. The separation d of the membranes 18 around the earlobe to which the ear clip 5 is attached must be accurately determined and maintained in order for the readings to be accurate and to avoid recalibration, and the membranes 18 must be fully parallel.

A simple spring clip that closes onto the ear lobe under influence of a spring, whose separation is determined by the thickness of the ear lobe and the strength of the spring, will have a varying separation and will not generate reproducible results. It is thus necessary to separate the earlobe engaging and clasping effect of the spring that enables the clip to be engaged on the ear lobe, and a separate means of controlling the separation of the jaws 20 when no external separating force is acting, and the jaws 20 of the clip 5 are attached onto the ear lobe by the spring.

FIG. 1 shows one position of the herein ear clip 5 wherein the jaws 20 of the shells 10, 12 are close together thereby bringing the membranes 18 into close proximity d, where the membranes 18 are in parallel with each other and are separated by a known and controllable gap. Typically, this is the operational position when the clip 5 is affixed on the earlobe of a subject. FIG. 2 shows the ear clip 5 in another position where the jaws 20 of the shells 10, 12 are separated by a larger gap. This would be the position, wherein the jaws 20 of the shells 10, 12 are sufficiently separated that the ear clip 5 may be attached to a thicker earlobe. The gap between the jaws may be varied over a range, typically of from about 3 mm to about 6 mm.

The gap may be controlled by an adjustment mechanism that includes a screw 38 that engages a hinge pin joint 22. FIGS. 1 and 2 show the hinge pin joint 22 fitted into an insert 9 in the lower shell 10.

Figure 3:
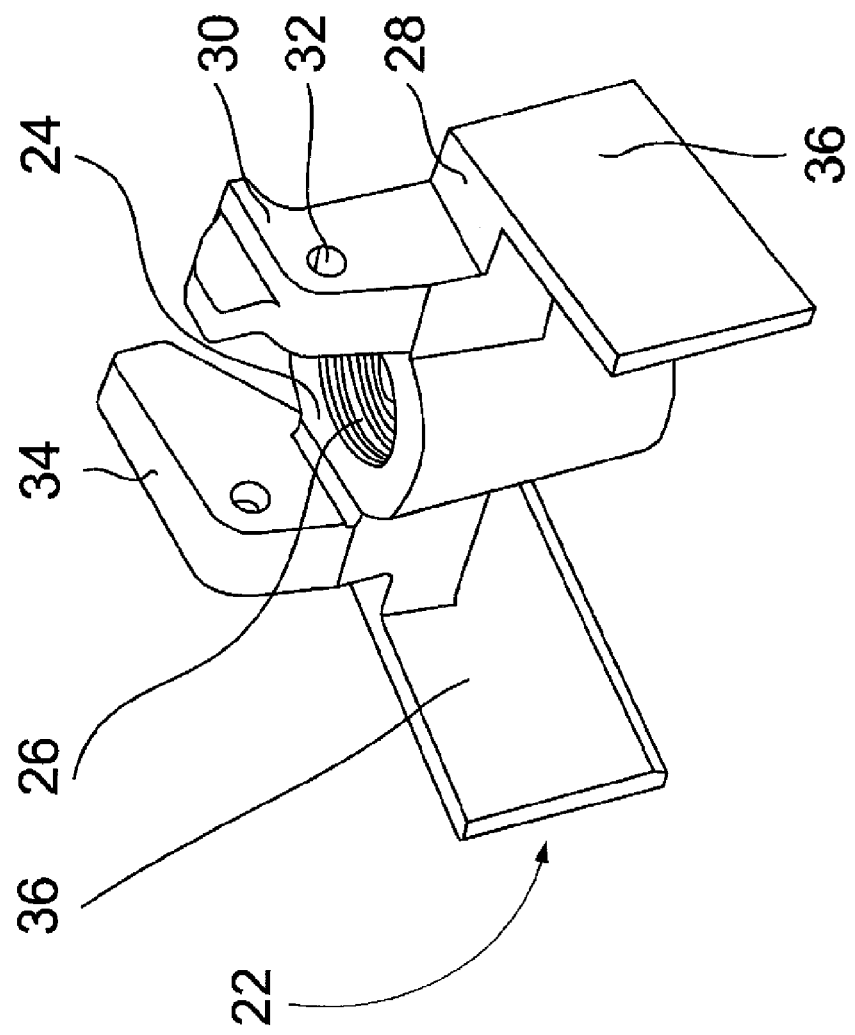
FIG. 3 is a top perspective view of one embodiment of the hinge pin joint.
Figure 4:
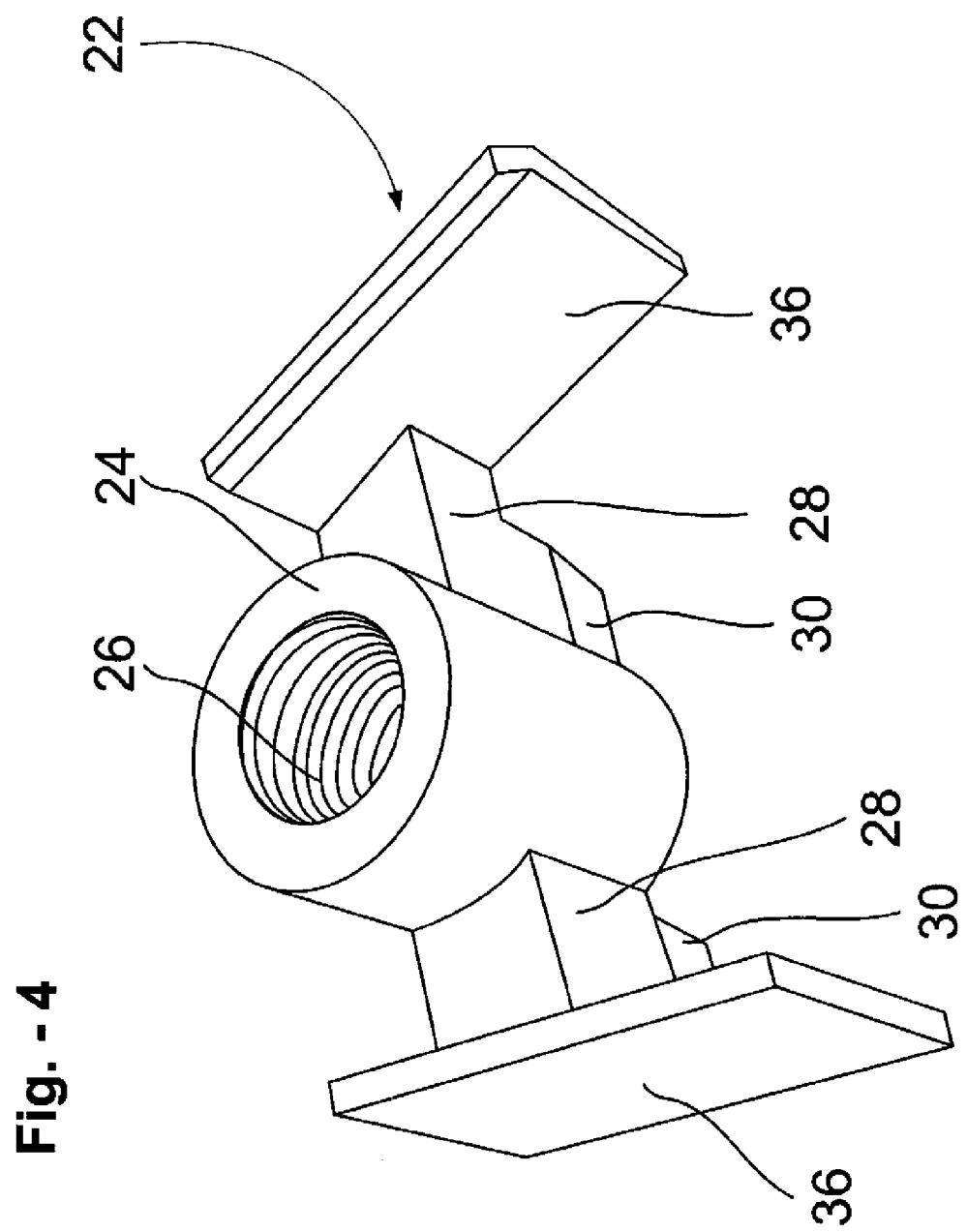
FIG. 4 is a bottom perspective view of the embodiment of FIG. 3.
Figure 5:
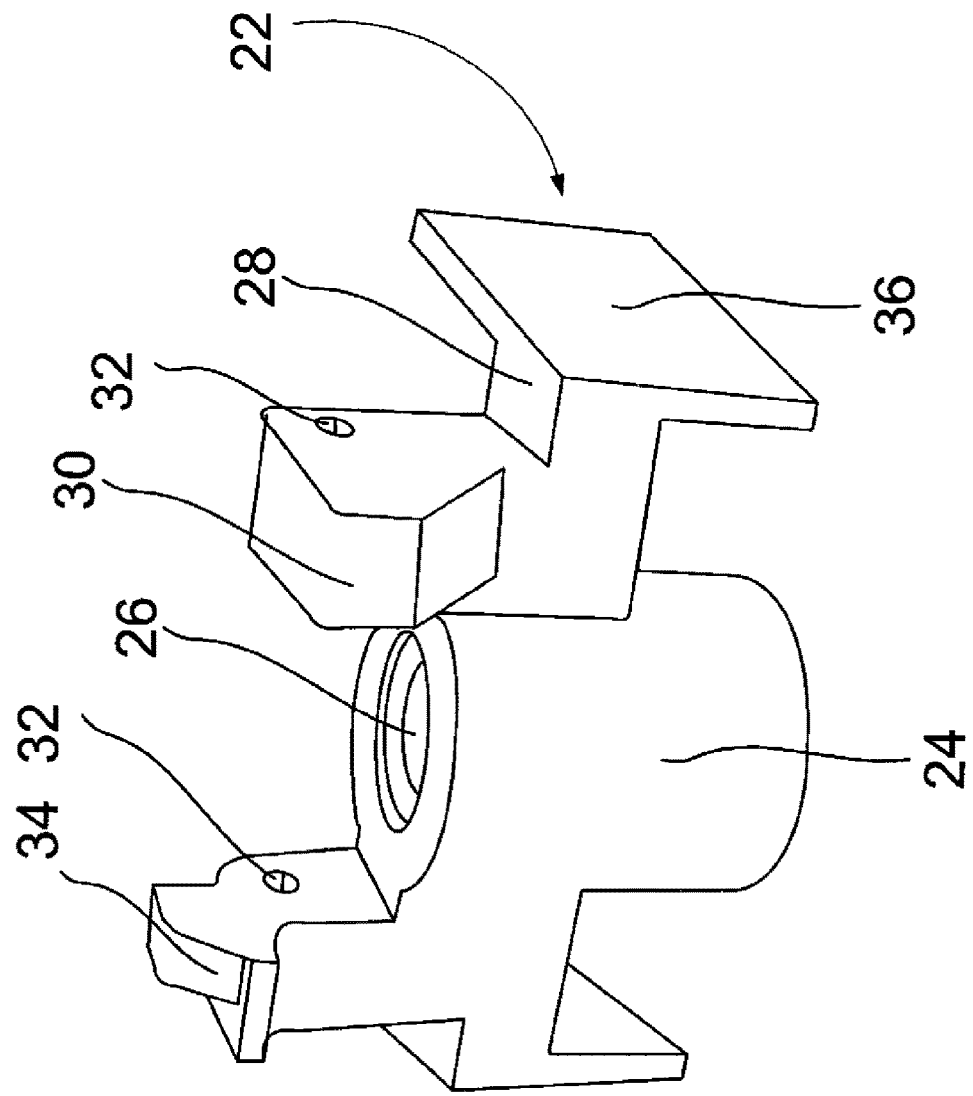
FIG. 5 is a rear perspective view of the embodiment of FIG. 3.

One embodiment of the hinge pin joint 22 is illustrated in FIGS. 3-5. A second, preferred embodiment of the hinge pin joint 122 is illustrated in FIGS. 15-21. The hinge pin joint 22 (122) together with the adjustment screw 38 shown in FIG. 6 allow precise separation of the jaws 20 of the shells 10, 12 and their precise, parallel alignment with respect to each other.

The upper shell 12 may pivot around an axle pin 50. The axle pin 50 is a central element, which allows precise pivoting of the shells 10, 12 with respect to each other so that the jaws 20 may be separated to allow the clip 5 to be securely attached to an ear lobe.

Figure 12:
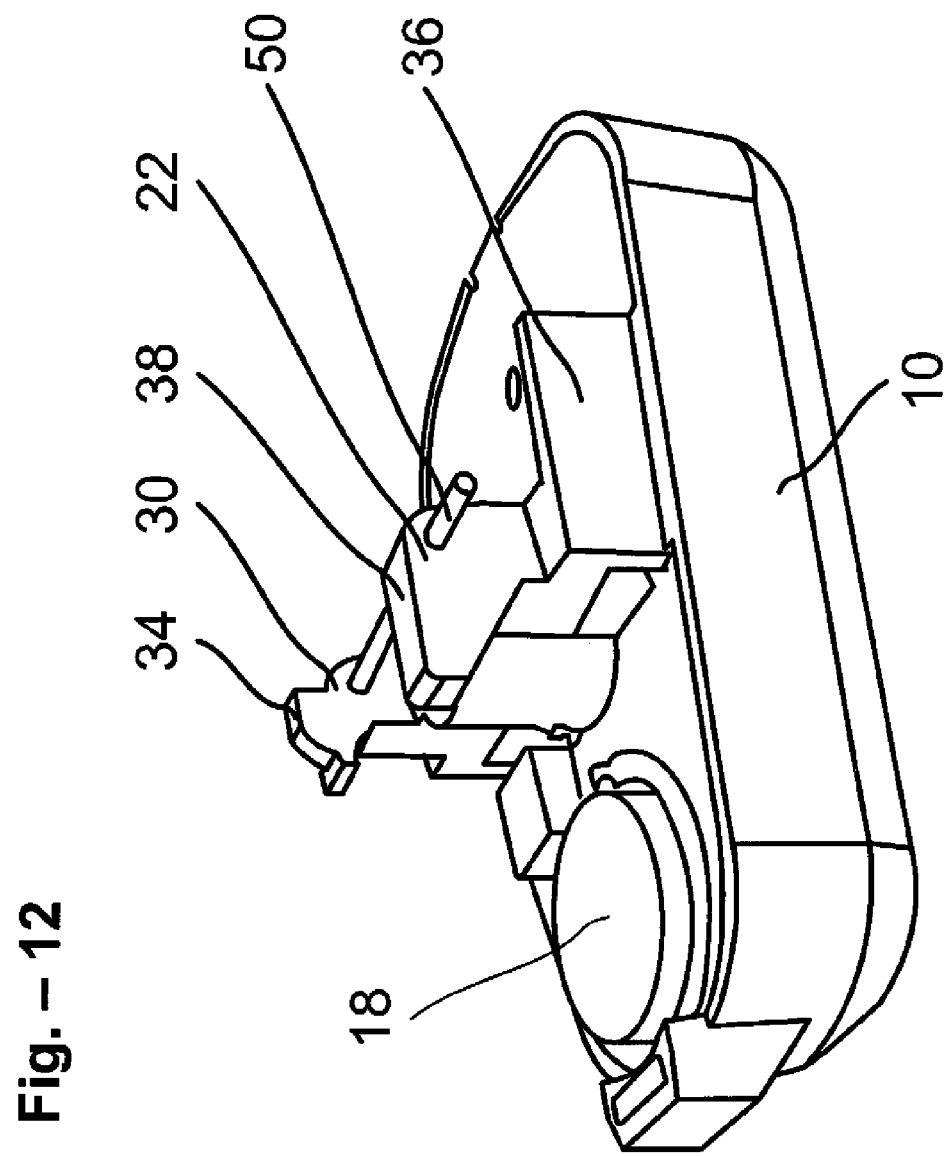
FIG. 12 is a side perspective view, of the lower shell and a second embodiment of the hinge pin joint from above.

With reference to FIGS. 3 to 5, in a first embodiment, the hinge pin joint 22 includes a base cylinder 24 with a threaded bore 26. Extending radially from the base cylinder 24 are radial arms 28. Pin supports 30 are affixed to the radial arms 28. The pin supports 30 have aligned axle bearing holes 32 for engaging an axle pin 50 (FIG. 12). The ear clip 5 includes a stop 34 that prevents the jaws from closing together beyond a parallel alignment. As shown in FIGS. 3-5, in one embodiment, the stop 34 may be part of a pin support. At the end of each radial arm 28, stabilizing wings 36 are provided. Preferably, the stabilizing wings 36 extend at an angle of more than 45° to the radial extensions 28. More preferably, the stabilizing wings 36 extend at an angle of 70° to 110° and, most preferably, the stabilizing wings 36 are approximately perpendicular to the radial extensions 28. In preferred embodiments, these wings 36 are plate-like, but in alternative embodiments, the wings may be rods or may any other useful and desirable shape. The stabilizing wings 36 may extend both forwards and backwards from the radial arms 28, and tightly fit into a correspondingly shaped housing within the injection moulded lower shell 10. In this manner, a tight fit is achievable using the ordinary tolerances for injection moulding, thereby enabling accurate alignment between the sensor components attached to the upper 12 and lower 11 shells.

Figure 16:
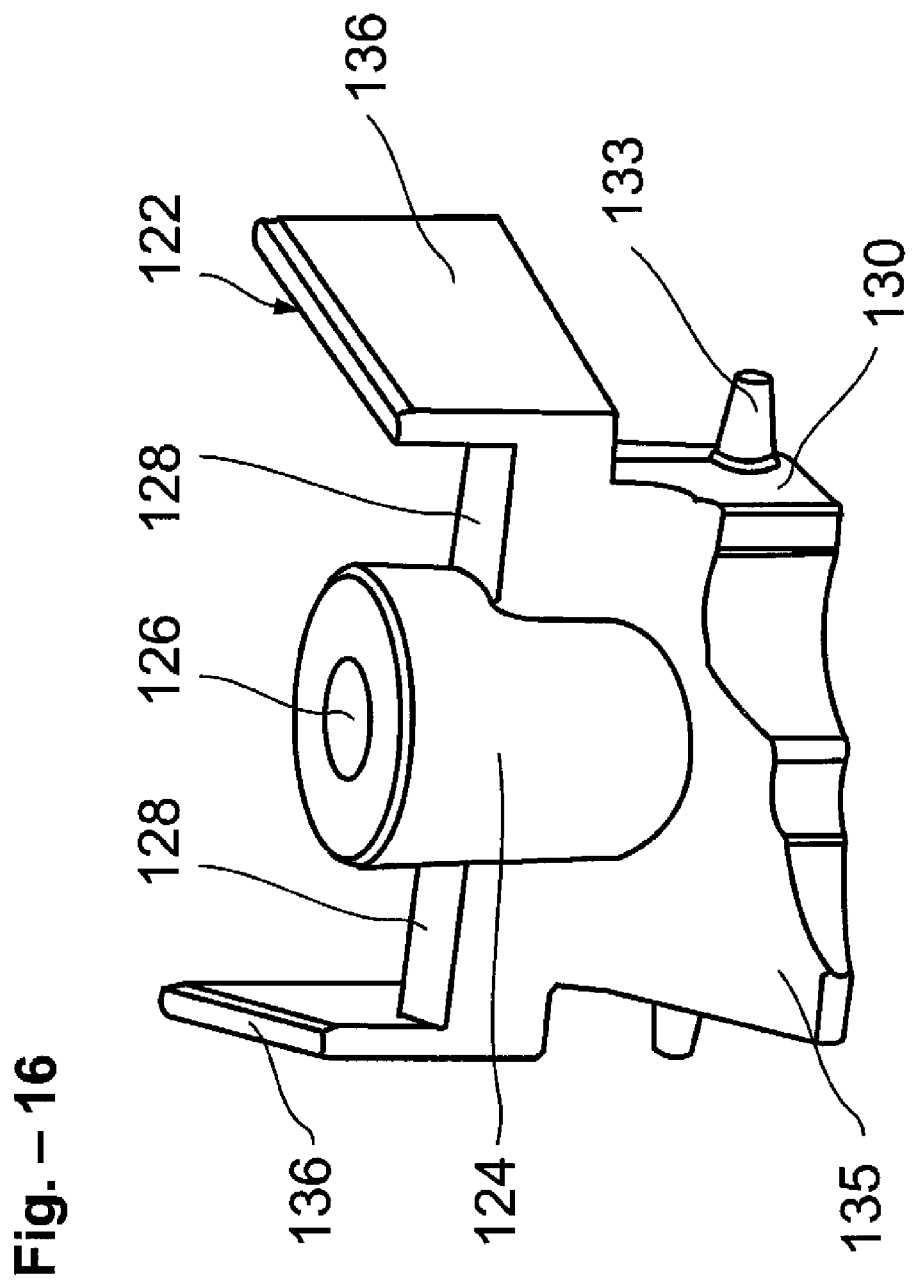
FIG. 16 is a perspective view of the preferred embodiment of the hinge pin joint.
Figure 17:
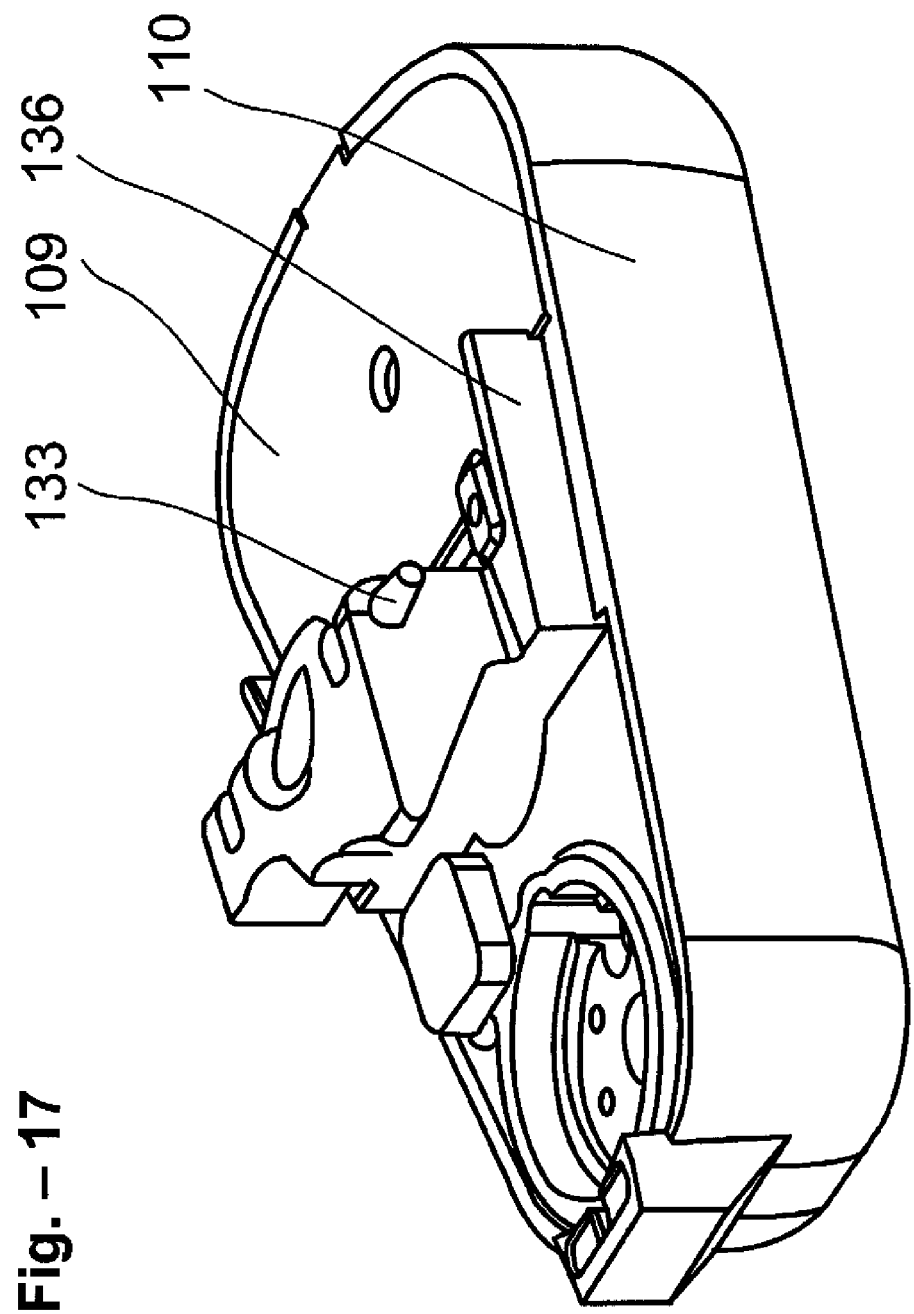
FIG. 17 is an exploded perspective view of a preferred embodiment of the lower shell, its cover and the hinge pin joint of the preferred embodiment.
Figure 18:
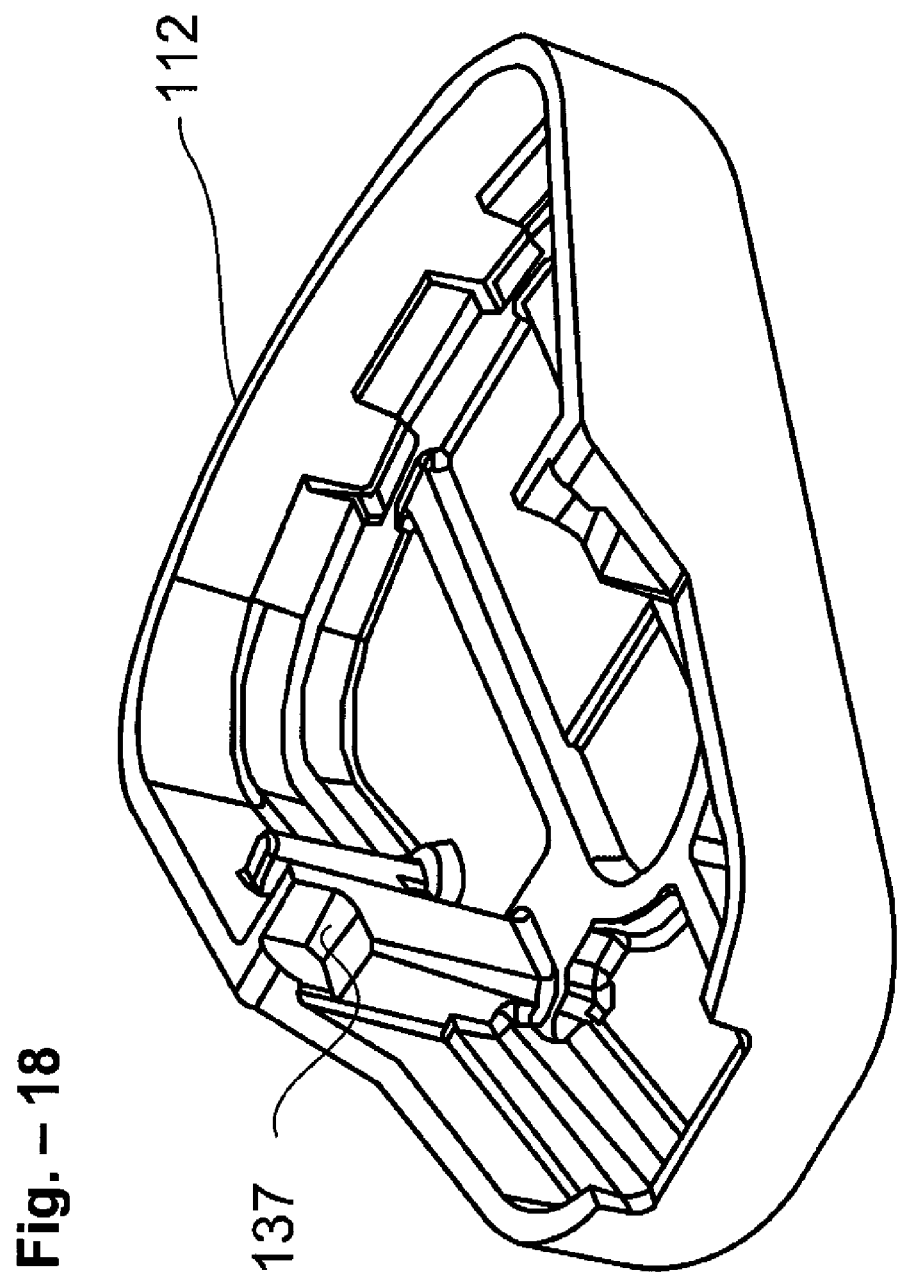
FIG. 18 is a perspective view of the under surface of the upper shell.
Figure 19:
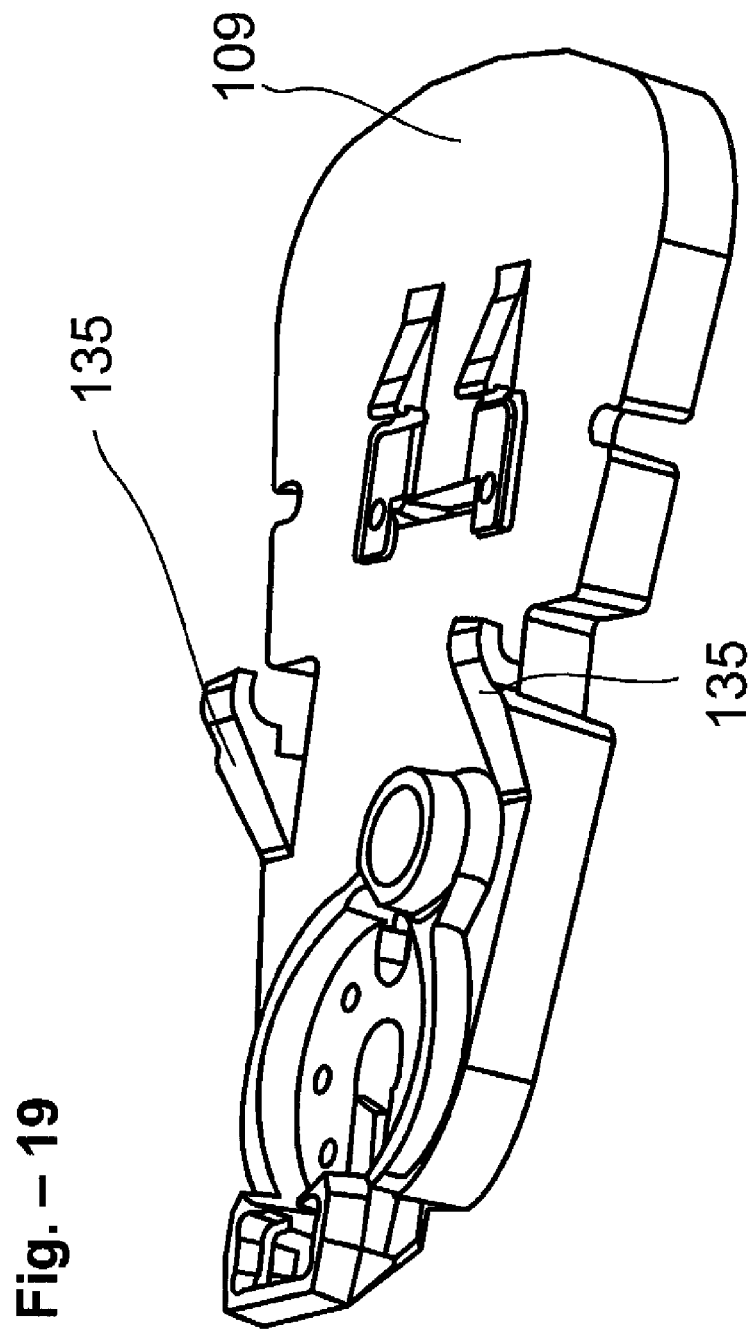
FIG. 19 is a perspective view of the insert of the lower shell.

With reference to FIG. 16, in a preferred embodiment, the hinge pin joint 122 includes a base cylinder 124 with a threaded bore 126. Extending radially from two sides of the base cylinder 124 are radial extensions 128. Pin supports 130 are provided on the radial extensions 128. In one embodiment, the pin supports 130 may include integral hinge pins 133. On one of the pin supports 130, a stop 135 is placed. At the end of each radial extension 28, support wings 136 are provided. In a preferred embodiment, the support wings 136 are plates, but in other embodiments, the support wings 136 may be rods or may assume some other useful and desirable shape.

Figure 20:
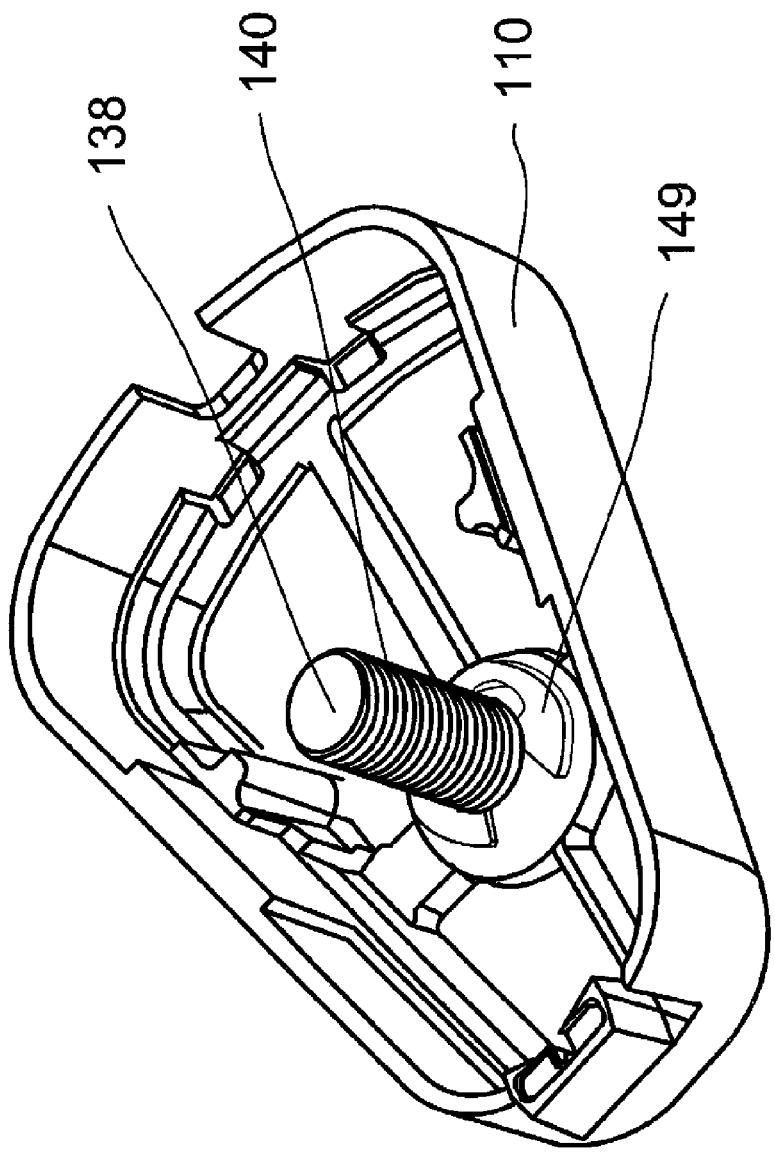
FIG. 20 is a perspective view of the under surface of the lower shell.
Figure 21:
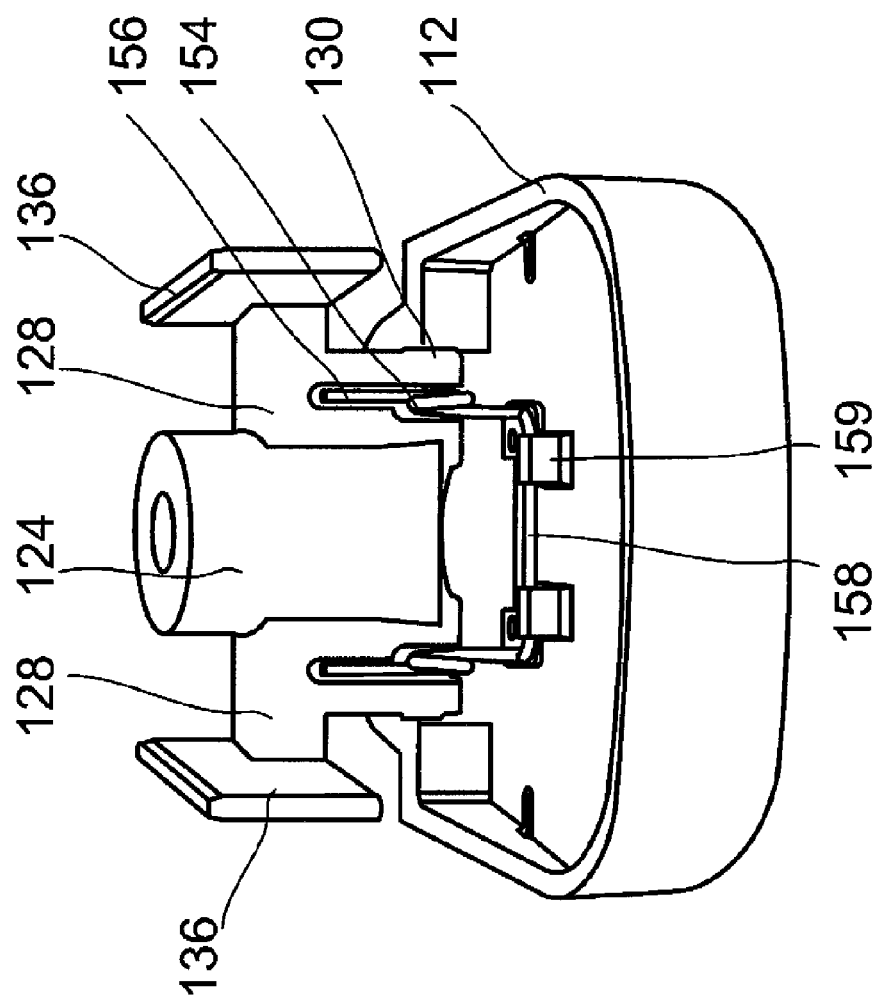
FIG. 21 is an end view, showing the preferred embodiment of the biasing spring, where for purposes of illustration, the spring has three turns.

In preferred embodiments, the adjustment means comprise an adjustment screw 138 as shown in FIG. 20 that screwingly engages the threaded bore 26, 126. Preferably, for attachment to an ear lobe, the step of the thread is 0.5 mm. For other embodiments, such as for other applications, other thread steps may be selected, depending on the size of the clip. The adjustment screw 138 has a threaded shank 40, 140 and an enlarged head 42 with a slot 48 for a screw driver, which may be a conventional slot or cross, a hexagonal head or a unique slot for a dedicated tool. The head 42 of the screw is typically counter sunk into the shell. To hold the screw 38 in place within the lower shell 10, a retaining washer clip 46, 149 may be used. The retaining washer 46, 149 is an open clip that slides onto the threaded shank of the adjustment screw 38. It may be fabricated from metal, for example.

Figure 6:
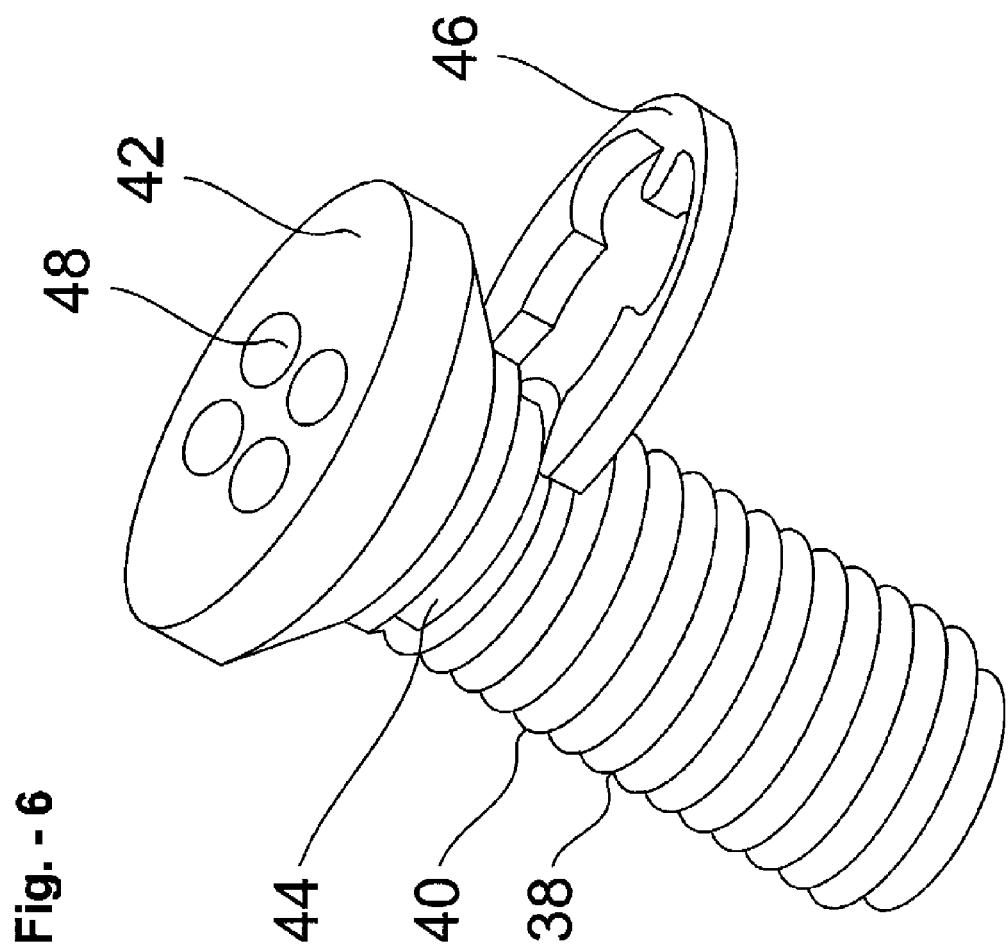
FIG. 6 is a perspective view of the adjustment screw with a retaining washer.

An alternate embodiment of the adjustment screw 38 is shown in FIG. 6. It is a standard screw 38 with a threaded shank 40 and an enlarged head 42 with a slot 48 therein for a tool or key.

Figure 11:
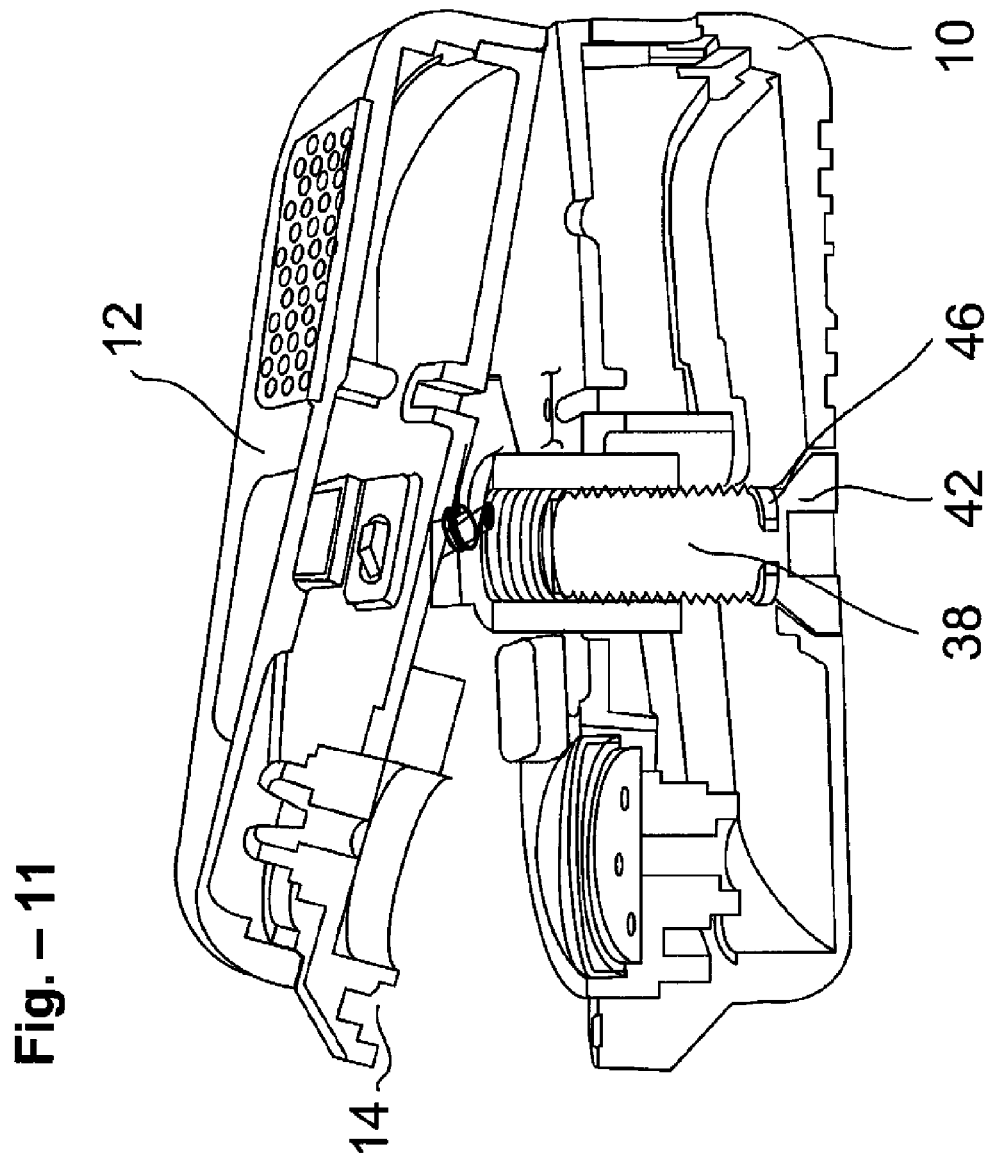
FIG. 11 is a view from the angle of FIGS. 1, 9 and 10, with the handles squeezed together and the jaws separated.

FIGS. 15-18 show the hinge pin joint 122 fitted into an insert 109 of the lower shell 10. The adjustment screw 38 is inserted through an opening in the lower shell 110 and is threaded into the lower end of the threaded bore 126 of the base cylinder 124. The adjusting screw is positioned so that the working ends (jaws) 20 of the upper and lower shells 10, 12 of the clip 5 are at an appropriate separation to engage a pateint's ear lobe securely enough for the clip 5 to be clipped in place, but loosely enough so as not to squash the capillaries of the ear lobe. Once calibrated to an appropriate separation, the clip may be opened by pressure to the grips 6, to separate jaws 20, but on release of squeezing pressure, the jaws return to parallel alignment at the set separation. FIG. 11 shows that the clip 5 may be adjusted by the adjusting screw 38 such that the distance between the sensors 18 in the jaws 20 can be increased or decreased. The adjustment screw 38 is provided with a locking washer 46 just below the head 42.

Figure 7:
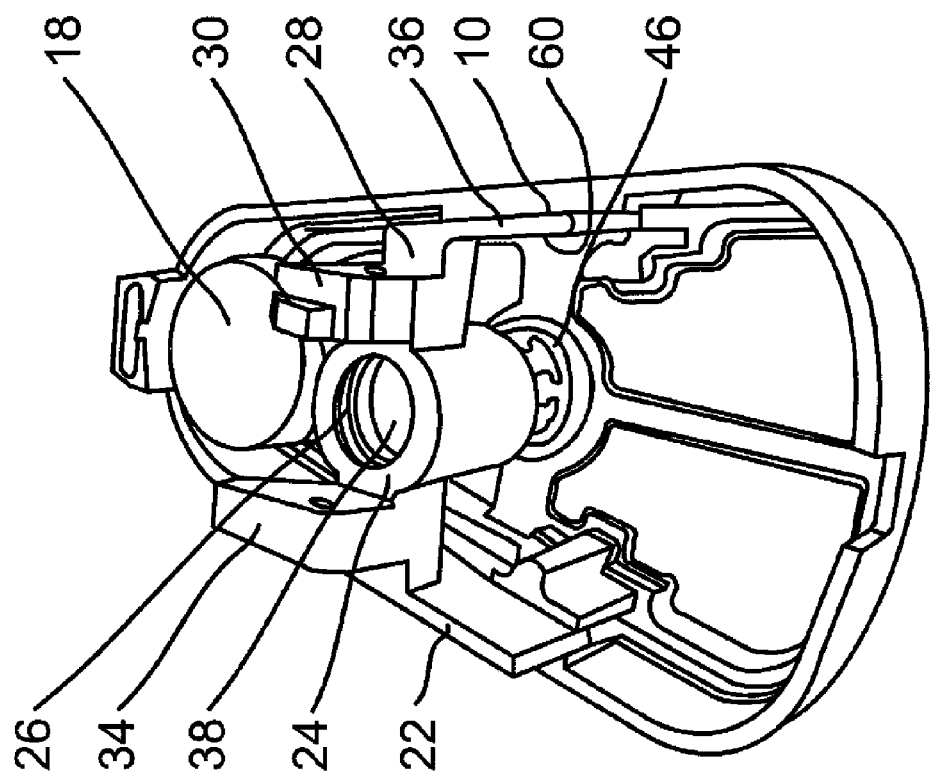
FIG. 7 is a perspective view of the inside of the lower shell of the clip from above, with upper shell and lower cover removed, showing the hinge pin joint and the adjustment screw.
Figure 8:
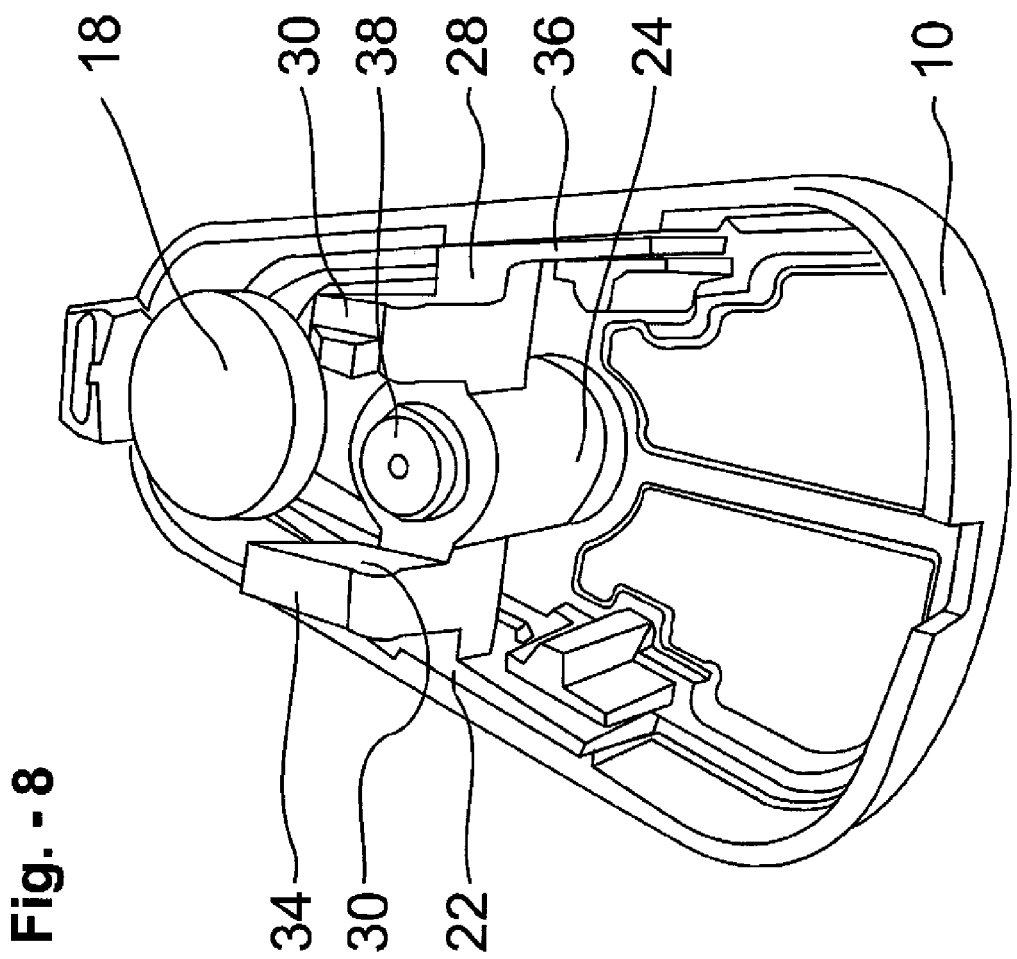
FIG. 8 is a perspective view from the angle of FIG. 7, showing the lower shell of the clip with the upper shell removed, and showing the hinge pin joint of FIG. 3-5 but with the adjustment screw of FIG. 6 fully closed by being fully threaded into the hinge pin joint.
Figure 9:
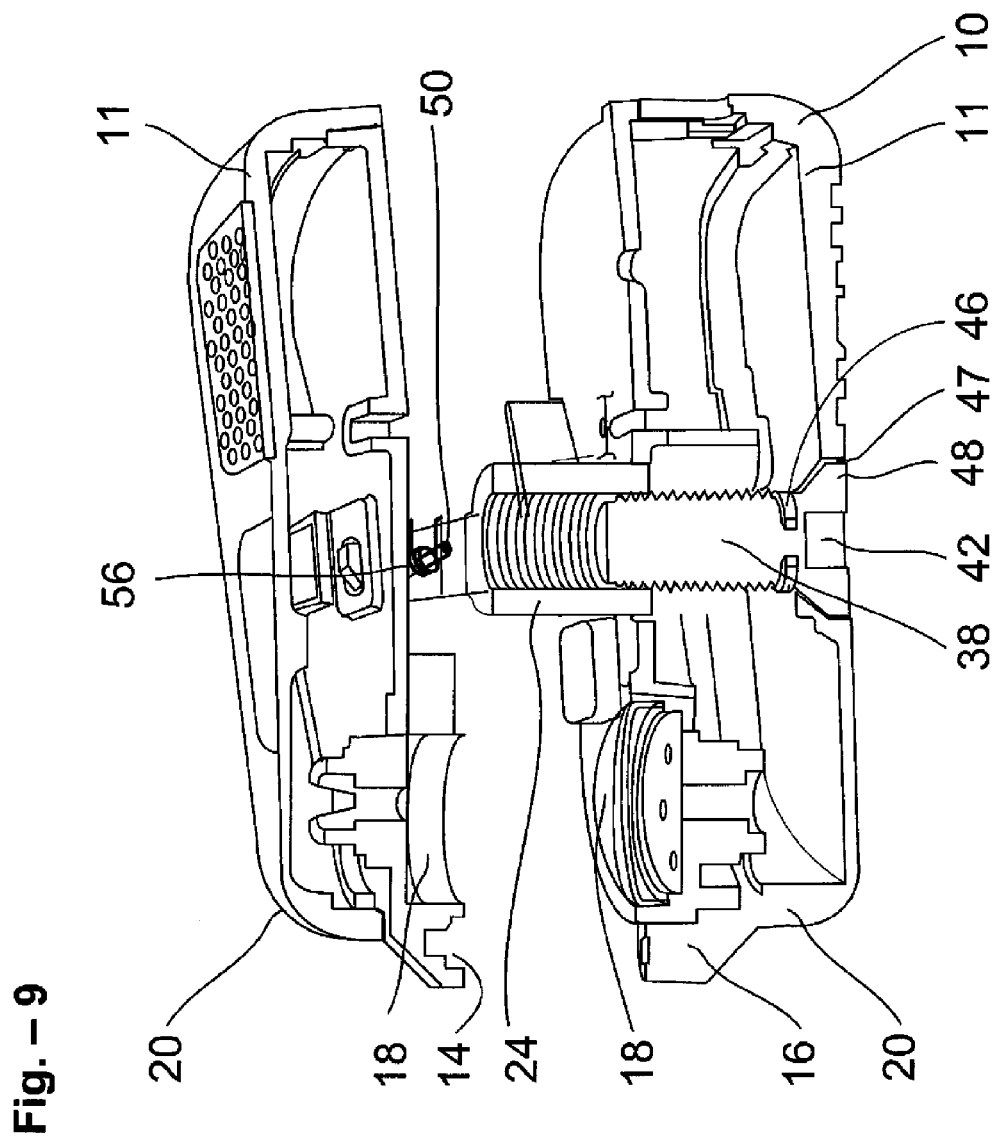
FIG. 9 is a cut away perspective view from the viewing angle of FIG. 1.
Figure 10:
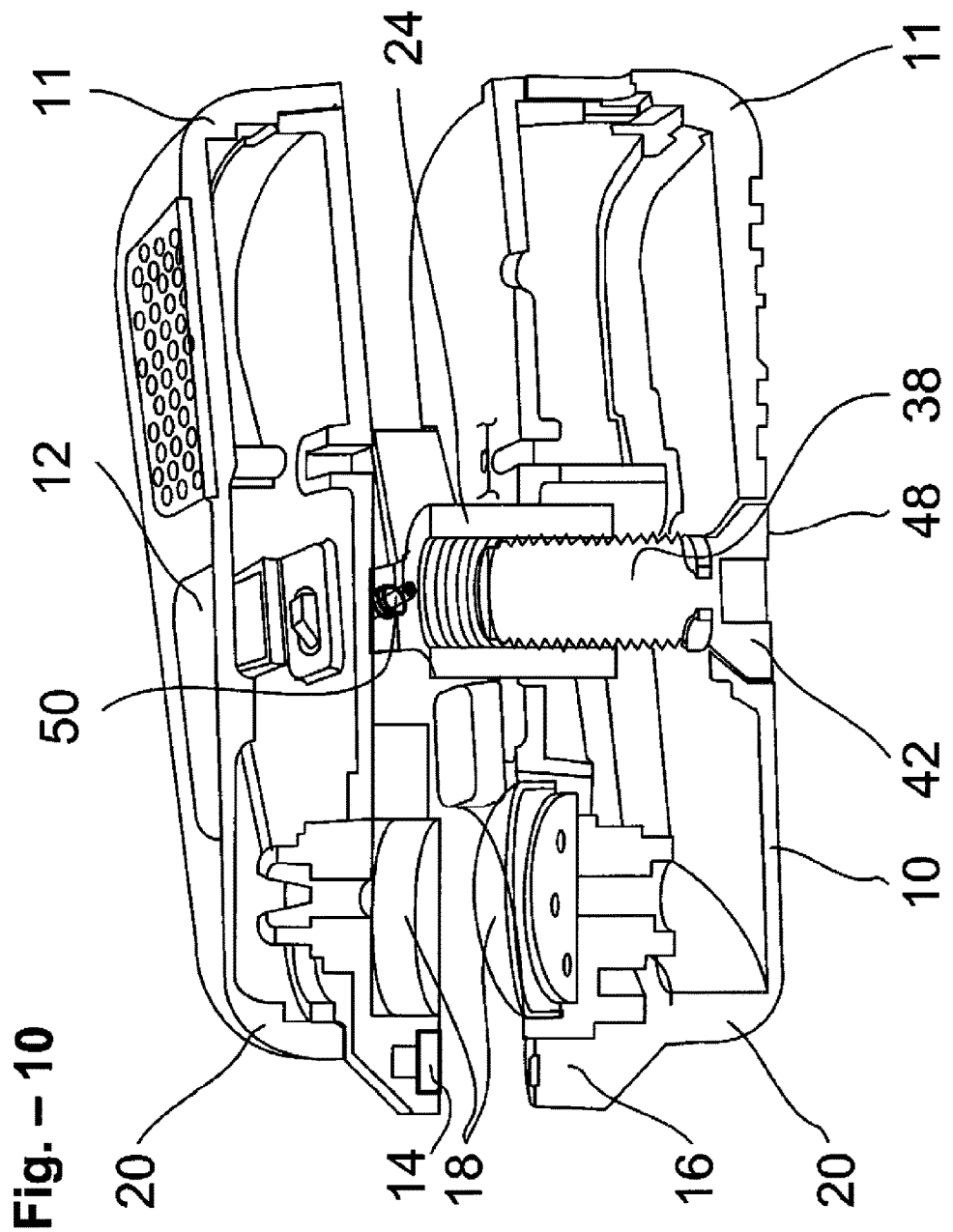
FIG. 10 is a view from the angle of FIG. 9, but showing the ends of the clip closer together.

For an alternative embodiment, FIGS. 7-9 show the hinge pin joint 22 fitted into the lower shell 10. The adjustment screw 38 is inserted through an opening 47 in the lower shell 10 and is threaded into the lower end of the threaded bore 26 of the base cylinder 24 of the hinge pin joint 22 (see FIGS. 1, 9, 10 and 11). The adjusting screw 38 is positioned (shown in FIG. 10) so that the working ends 20 of the upper and lower shells 12, 10 of the clip are close together. FIG. 9 shows that the clip 5 may be adjusted by using the adjusting screw 38 in a way that the separation distance between the sensors is increased.

In the preferred embodiment, the axle pin 133 on the hinge pin joint 22 is held by bearings consisting of a socket having one part 135 on the lower cover 109 (FIGS. 15, 19), and a second part 137 on the upper shell 112 (FIG. 18) that close around the pin 133 to hold it tightly in place so that the upper and lower shells 10, 12 are held together by the pin 133. In this manner the upper shell 112 pivots about the pin 133 and pivots with respect to the lower shell 110.

Figure 13:
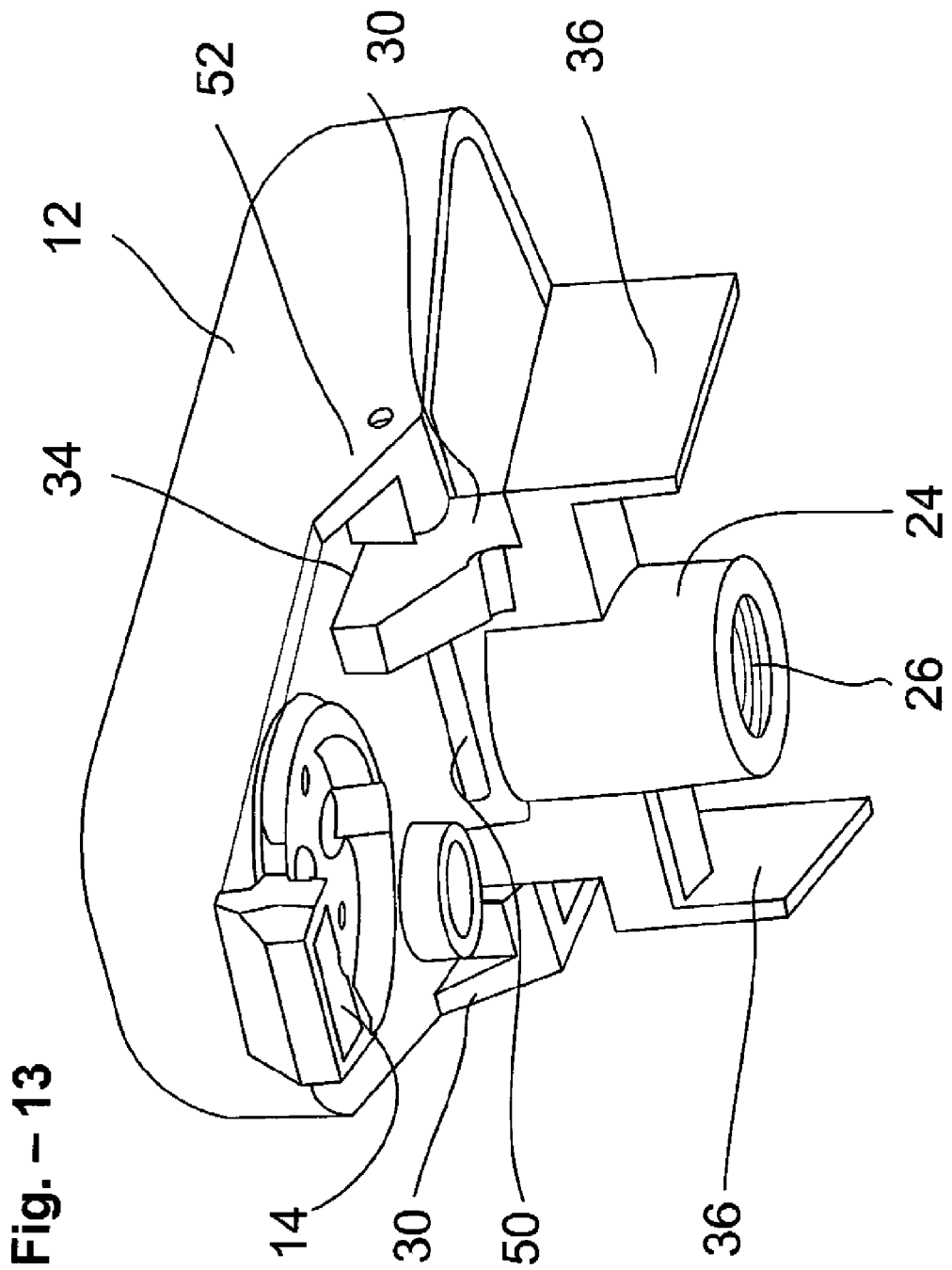
FIG. 13 is an enlarged perspective view of the upper shell from below.

In connection with the embodiment shown in FIG. 12, an axle pin 50 may be inserted into the aligned openings 32 of the pin supports 30 of the hinge pin joint 22. The ends of the axle pin 50 are engaged by holes in mountings 52 on the upper shell 12 (see FIG. 13). In this manner the upper shell 12 may be pivoted about the axle pin 50 with respect to the lower shell 10.

A biasing spring 54 may be used to maintain the shells 10, 12 in a closed position. In one embodiment, shown in FIGS. 14 and 21, the ends 56 of the biasing spring 54 exert a force against the back of the pin supports 30 and the central portion (or bow) 58 of the spring 54 exerts a force against the inner surface of the upper shell 12. (FIG. 21) By pressing on the handle ends 11 of the shells 10 and 12, the resistive force of the spring 54 is overcome, and the working ends (jaws) 20 of the shells 10 and 12 are separated beyond the predefined parallel separation. When pressure is released, the spring 54 restores the working ends 20 of the shells back to their predefined position, with the spacing set by the adjustment means, typically the screw 38. In some embodiments, it may be desirable to provide clips 159 (FIG. 21) to engage and hold the central region (or bow) 58 of the spring 54.

Figure 14:
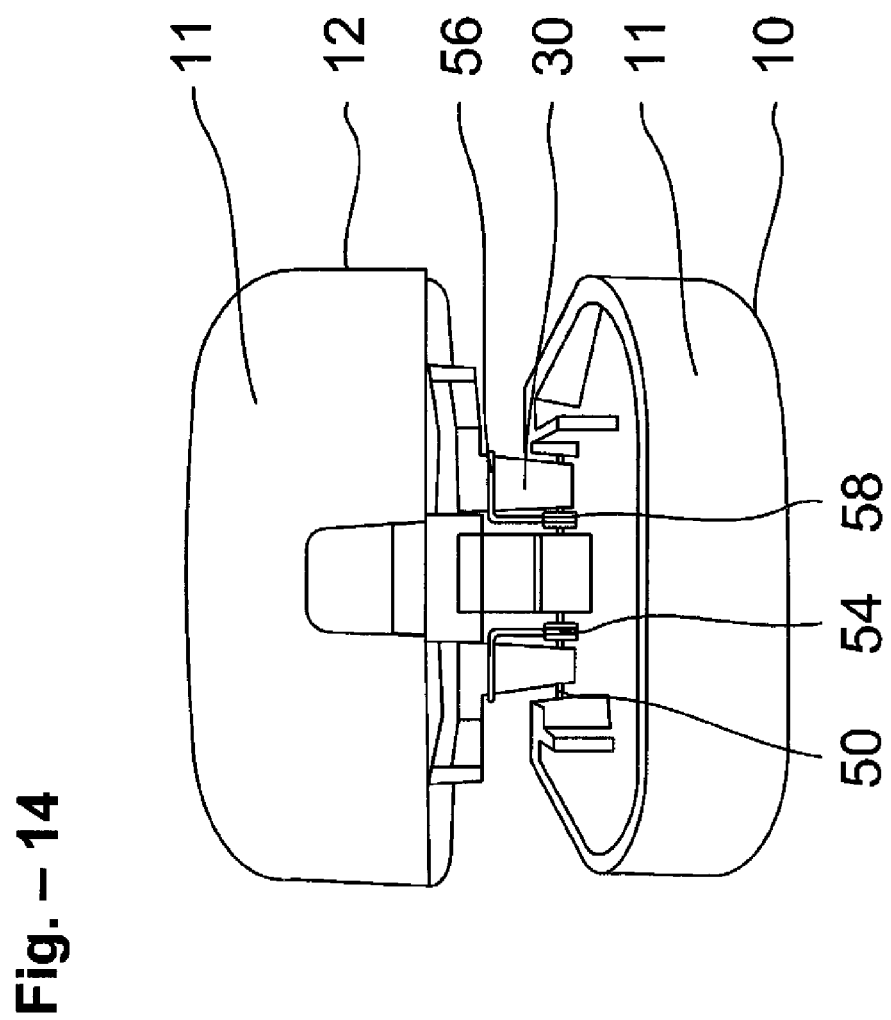
FIG. 14 is an end view, showing one embodiment of the biasing spring.
Figure 15:
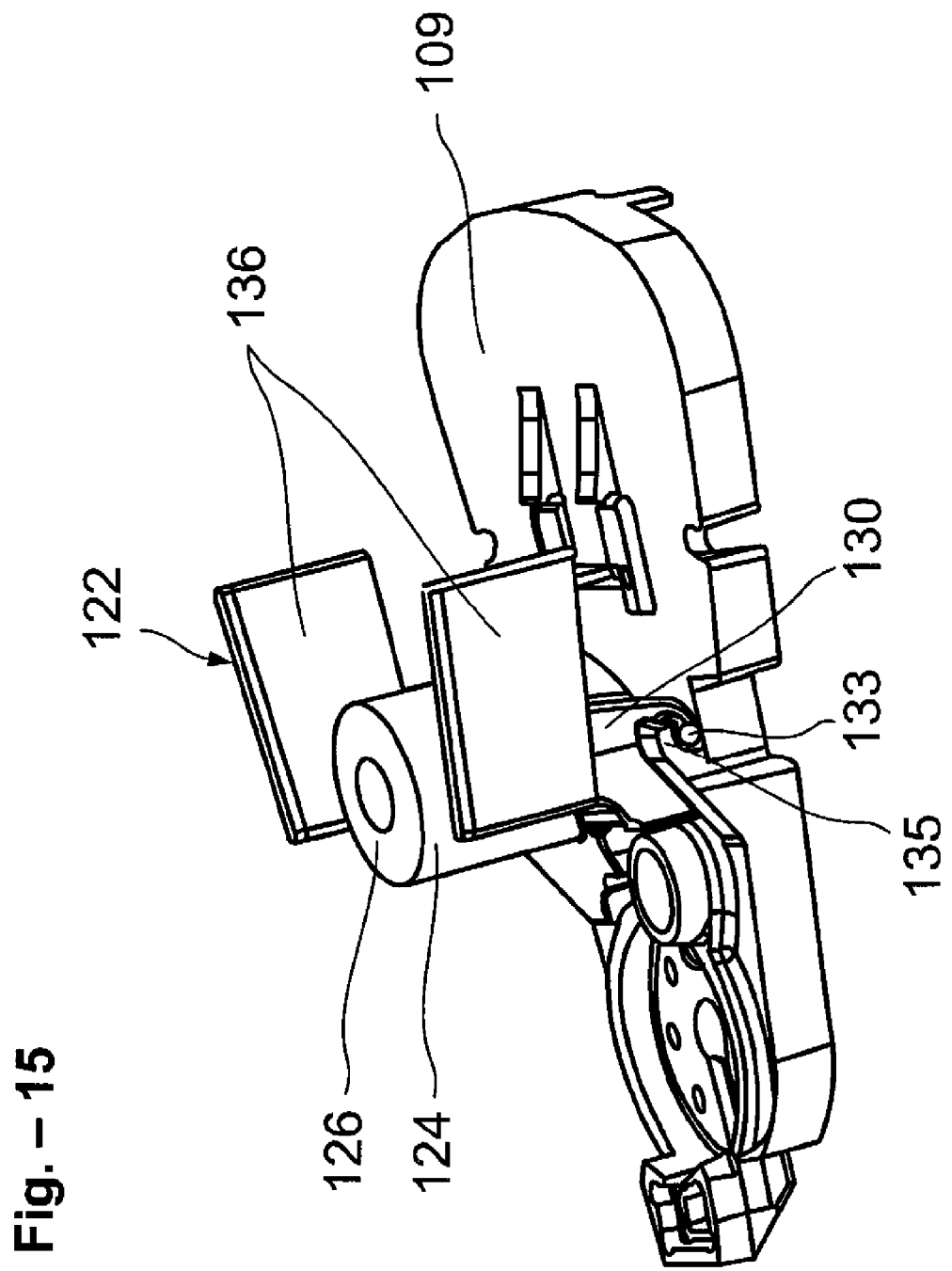
FIG. 15 is a perspective view of a preferred embodiment of the hinge pin joint mounted on an insert of the lower shell.

In one embodiment, the coiled biasing spring 54 may be wrapped around the hinge pin 50 to maintain the shells 10, 12 in their predetermined parallel and close position. Ends 56 of the spring bear against the back of the pin supports 30 and the central region (a bow) 58 in the middle of the spring bears against the inner surface of the upper shell 12 (FIG. 14). By pressing on the handle ends 11 of the shells 10 and 12, the force of the spring 54 is overcome, and the jaws 20 of the shells 10 and 12 are moved apart. When pressure is released, the spring 54 restores the working ends or jaws 20 of the shells 10, 12 back to their predefined spacing.

As shown in FIG. 7, the hinge pin joint 22 may be situated within an appropriately shaped cavity of the lower shell 10 so that it cannot rotate or wiggle about, but may be moved up and down to some extent within the confines of the cavity of the lower shell 10. Guidance structures 60 are built into the surface of the lower shell 10 to semi-rigidly hold the hinge pin joint 22 in place, but with sufficient clearance for the hinge pin joint 22 to be able to move relative to the lower shell 10.

By means of the hinge pins 133 (or the pin 50) the hinge pin joint 22 (122) is fixedly secured to the upper shell 12 (122) by virtue of the ends of the pin(s) being held in the upper shell 12 (122) (either in hinge socket 35 or the mountings 52).

The position of the screw 38 within the threaded bore 26 of the base cylinder 24 of the hinge pin joint may be adjusted with an appropriate screwdriver for engaging the screw head 48. Optionally, a special screw head 48 is used, that requires a dedicated screwdriver tool.

Adjustment of the screw 38 moves the hinge pin joint 22 (122) up and down with respect to the lower shell 10 (110). Since the screw 38 is fixedly positioned in the lower shell 10 (110) by the washer clip 46, and the hinge pin joint 22 (122) is fixedly positioned in the upper shell 12 (112), rotation of the screw 38 within the bore causes vertical displacement of the shells 10 (110), 12 (112) relative to each other, and adjusts the separation of the jaws 20. Turning the screw 38 clockwise or anticlockwise threads it further into or out from the bore 26 of the hinge pin joint 22 and adjusts the separation of the shells 10 (110), 12 (112) relative to each other. Hence rotation of the screw 38 allows the user to adjust the distance between the jaws 20 of the two shells 10 (110), 12 (112) (and thus between membranes 18 and other sensors, by increasing or decreasing their separation. This allows a precise adjustment of the distance between the jaws 20 of the shells 10 (110), 12 (112).

The pitch of the thread on the screw 38 is selected precisely so that a single full turn of the screw 38 translates to a known precise distance. In one embodiment, a 360° turn corresponds to a separation of 0.4 mm between the working ends of the shells 10, 12. Therefore, by careful rotation of the screw, the user may precisely determine the distance between the sensors on the working ends (jaws) 20 of the shells 10, 12. It is relatively easy to give a quarter turn, half turn or three quarter turn to the screw to thereby separate the jaws 18 of the shells 10, 12 by 100 microns at a time. Smaller turns are also possible. Optionally, the underside of the lower shell 10 is marked so that known small adjustments may be made more easily and accurately. It will be appreciated that other threads could be utilized, and a single full turn may be set to other small amounts, such as 0.3 or 0.5 mm etc.

As aforesaid, in some embodiments, extending laterally from the pin supports 30 of the hinge pin joint 22 are stops 34. These stops 34 prevent the jaws 20 from closing completely and keep the jaws, when no squeezing pressure is applied to the handles 11, in parallel with each other at a separation controlled by the turning of the screw 28 to maintain the proper parallel relationship between the upper and lower shells 12, 10 when the clip 5 is closed and in its working position, thereby making the arrangement more stable. A preferred embodiment shown has one stop 34 on just one of the pin supports 30, but in other embodiments, two stops may be provided.

The specially formed part (hinge pin joint) 22 includes the threaded bore 24 for the screw 38 that is used to adjust the separation between the working ends or jaws 20 of the shells 10, 12 (and thus the sensors), when handles 11 are released. Stabilizing wings 36, typically formed as plates, function in the guide structure 60 of the lower shell 12. These stabilizing wings 36 may be arranged at an angle so that they are directed to a meeting point along the lateral axis of the clip 5, perpendicular to the hinge pins 33 (50). Alternatively, the stabilizing wings 36 may be strictly parallel to the axis on which the height or the distance between the sensors is adjusted. Thus, referring to the axis of the adjusting screw 38 as the Z axis, and the axis of the hinge pin 50 (133) as the y axis, the stabilizing wings 36 (136) are symmetrically arranged and may converge or be parallel to the x axis that is perpendicular to the z and y axes, thus defined. The stabilizing wings 36 (136) are tightly engaged by corresponding slots in the upper shell 10 and, by using regular manufacturing tolerances, looseness about the hinge, as is typical of regular clips, is avoided and accurate alignment of the sensors 18 is enabled. The two stabilizing wings 36 (136) may form together an interrupted v-shaped form that fits in the guide structure of the upper shell 12, having the same angle.

An advantage of the stabilizing wings 36 (136) being slightly converging is that the hinge pin joint 22 (122) will thereby generally adjust itself within the slot of the upper shell 12 to maintain proper positioning despite regular manufacturing tolerances or slight inaccuracies during fabrication. Where, due to production inaccuracies, the parts with the guide structure are wider-than the theoretical dimension, the hinge pin joint 22 (122) with the two stabilizing wings 36 (136) that are arranged in a v-shape would move further towards the tips and would then adjust the part there. If the part with the guide structure in it is smaller than the theoretical dimension, then the part with the two stabilizing wings 36 (136) would move a bit away from the tips until it rests at the exact location.

The same true when the part with the two plates is bigger or smaller than the theoretical dimension. Here also the stabilizing wings 36 (136) would find the exact point, where they fit their socket precisely, by moving along the x-axis. The amount of movement along the x-axis is dependent on the degree of accuracy of the final part. This angle determines how much the part would then be out of centre relative to the centre point of the screw 38 that adjusts the two halves of the clip 5 along the z-axis. Inaccuracies along the y-axis are also completely compensated for with this construction.

It will be appreciated that if the thread 26 for the bore 24 where the screw 38 is cut in at the end of the assembly process of the clip 5, after the montage, then the thread 26 will always be correctly centred.

The use of plates for the stabilizing wings 36, instead of, for example four rods or pins, leads to high accuracy and stability about the axle pin 50 (133). Such plate like stabilizing wings 36 have a maximum contact surface for their form where the plates are leaning against the guide structure. The maximum contact surface also leads to maximum support from the guide structure on the plates. Rods, for example, could bend into either the direction of the x- or the y-axis. The converging of the plates stands with the wall of either the right side or the left side with its complete surface and with a wall that stands with its cross-section against the force or partial vector of this force against any bending in either x- or y-direction.

Because the two stabilizing wings 36 are on the outside and are distanced from the adjustment screw 38, they have maximal leverage against any bending around the z-axis and/or along the x-axis. It will be appreciated that possible bending along the y-axis is not usually a problem because the stop 34 provides additional support to the clip in this direction. That would mean that the plates have otherwise run along the whole length of the clip 5. This bending moment is in the direction of the rotation around the hinge of the two halves of the clip 5 and is less critical, because the stop 34 provides additional support to the clip 5 in this direction.

Because the two stabilizing wings 36 are close to the outer edges of the clip 5 and separated as far as possible from the adjustment screw 38, they require a minimum of additional material for the guide structure and leave a maximum of space for the electronic components to be packed into the clip 5. The two converging stabilizing wings 36 are connected to the threaded bore 24 for the adjusting screw 38 by radial arms 28 that extend from the threaded bore 24.

The convergence also helps in production where it is generally necessary to add at least a two degrees angle to help remove parts from their molds. The converging shape allows the stabilizing wings 36 to remain straight, when the parting line is positioned along the y-axis.

Figure 22:
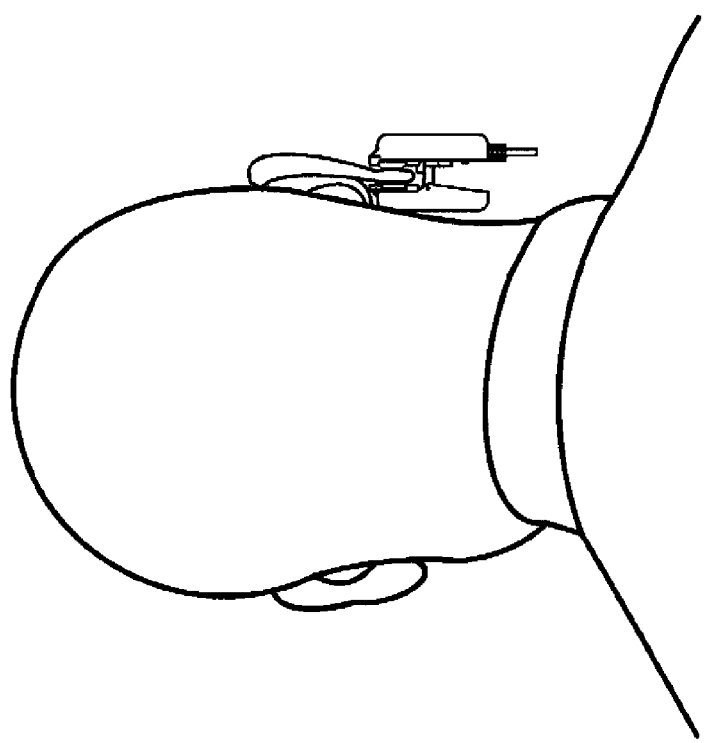
FIG. 22 is a schematic illustration of an ear clip of the invention clipped onto a patient's earlobe.

With reference to FIG. 22, an ear clip of the invention clipped onto a patient's earlobe is shown.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:
1. A clip comprising;
   an upper shell;
   and a lower shell, coupled together around a hinge pin, the upper and lower shells having a pair of jaws on a first side of the hinge pin, and handles for squeezing together to separate the jaws on a second side of the hinge pin; a biasing spring to oppose the squeezing together of the handles and to urge the jaws together;
   at least one stop to prevent the jaws from closing completely and to keep the jaws in parallel alignment when no force is applied to handles to overcome the biasing force of the spring;
   and an adjustment mechanism to adjust the separation of the jaws, wherein the adjustment mechanism comprises an adjustment screw,
   a washer clip,
   and an insert;
   said adjustment screw comprising a screw head and a threaded shank, the shank being pushed through a clearance hole in the lower shell, the adjustment screw being held in place around the lower shell by the washer clip, and the insert for fitting into a recess in the upper shell, said hinge pin being attached to said insert;
   said insert comprising a central block with a tapped hole therein, radial arms extending from the central block, and stabilizing wings integrally cast with the central block and radial arms, the stabilizing wings at an angle to the radial arms; said stabilizing wings for engaging the upper shell in accurate alignment with the lower shell;
   wherein the tapped hole is for receiving the adjustment screw such that the tapped hole and adjustment screw enables adjustment of the separation between the jaws of the upper shell and the lower shell when biasing effect of the biasing spring is not opposed by a squeezing pressure on handles.
2. The clip of claim 1 for clipping onto an ear lobe.
3. The clip of claim 2 further comprising blood parameter sensors mounted in said jaws.
4. The clip of claim 1 wherein the stabilizing wings are plates that have an axis that is parallel to an axis of the screw.
5. The clip of claim 4, wherein the stabilizing wings converge slightly towards an axis that is mutually perpendicular to the axes of the hinge pin and the axis of the adjustment screw.
6. The clip of claim 1 wherein the hinge pin is integral to the insert.
7. The clip of claim 1 wherein the hinge pin engages holes in said insert and holes in said upper shell to connect said upper shell to said insert.
8. The clip of claim 1 wherein the stop is a part of the insert.
9. The clip of claim 1 wherein the stop is part of the lower shell.
10. The clip according to claim 1 wherein said biasing spring is a helical spring and ends of said biasing spring bear against the back of the pin supports and middle section of said spring bears against an inner surface of said upper shell to urge jaws together.
11. The clip according to claim 1 wherein said biasing spring is wrapped around said hinge pin.
12. The adjustment mechanism of claim 1, wherein the screw is locked to one shell with a washer clip that slides onto and springingly engages shank of said screw.

* * * * *